US010632116B2

(12) United States Patent
Hansen et al.

(10) Patent No.: US 10,632,116 B2
(45) Date of Patent: Apr. 28, 2020

(54) COMBINATIONS OF SEROTONIN RECEPTOR AGONISTS FOR TREATMENT OF MOVEMENT DISORDERS

(71) Applicant: Contera Pharma A/S, København (DK)

(72) Inventors: John Bondo Hansen, Copenhagen Ø (DK); Mikael S. Thomsen, Hvidovre (DK)

(73) Assignee: Contera Pharma A/S, København (DK)

(*) Notice: Subject to any disclaimer, the term of this patent is extended or adjusted under 35 U.S.C. 154(b) by 66 days.

(21) Appl. No.: 14/937,286

(22) Filed: Nov. 10, 2015

(65) Prior Publication Data
US 2016/0058762 A1 Mar. 3, 2016

Related U.S. Application Data

(63) Continuation of application No. 13/879,128, filed as application No. PCT/DK2011/050383 on Oct. 13, 2011, now Pat. No. 9,186,359.

(60) Provisional application No. 61/491,945, filed on Jun. 1, 2011, provisional application No. 61/393,545, filed on Oct. 15, 2010.

(30) Foreign Application Priority Data

Oct. 15, 2010 (DK) .................. 2010 70441

(51) Int. Cl.
A61K 31/506 (2006.01)
A61K 31/422 (2006.01)
A61K 31/454 (2006.01)
A61K 31/4545 (2006.01)
A61K 31/496 (2006.01)
A61K 31/505 (2006.01)
A61K 45/06 (2006.01)
A61K 31/165 (2006.01)
A61K 31/198 (2006.01)

(52) U.S. Cl.
CPC .......... A61K 31/506 (2013.01); A61K 31/165 (2013.01); A61K 31/198 (2013.01); A61K 31/422 (2013.01); A61K 31/454 (2013.01); A61K 31/4545 (2013.01); A61K 31/496 (2013.01); A61K 31/505 (2013.01); A61K 45/06 (2013.01)

(58) Field of Classification Search
None
See application file for complete search history.

(56) References Cited

U.S. PATENT DOCUMENTS 3,717,634 A 2/1973 Wu et al.
3,976,776 A 8/1976 Wu et al.
4,166,452 A 9/1979 Generales, Jr.
4,182,763 A 1/1980 Casten et al.
4,265,874 A 5/1981 Bonsen et al.
4,356,108 A 10/1982 Schwab et al.
4,438,119 A 3/1984 Allen et al.
4,640,921 A 2/1987 Othmer et al.
4,687,772 A 8/1987 Alderdice
4,777,173 A 10/1988 Shrotryia et al.
5,185,329 A 2/1993 Gawin et al.
5,431,922 A 7/1995 Nicklasson
5,466,699 A 11/1995 Robertson et al.
5,484,788 A 1/1996 Sharpe et al.
5,633,009 A 5/1997 Kenealy et al.
5,637,314 A 6/1997 Sharpe et al.
5,705,506 A 1/1998 Merlet et al.
6,150,365 A 11/2000 Mayol
6,432,956 B1 8/2002 Dement et al.
6,750,237 B1 6/2004 Dearn et al.
7,220,767 B2 5/2007 Dearn et al.
8,329,734 B2 12/2012 Aung-Din
2007/0173536 A1 7/2007 Van Der Schaaf et al.
2007/0249621 A1 10/2007 Wolf et al.
2008/0226715 A1 9/2008 Cha et al.
2008/0227813 A1* 9/2008 Barber ................. A61K 31/165
514/318
2010/0105783 A1 4/2010 Lee et al.
2011/0318321 A1 12/2011 Selva et al.
2014/0221385 A1 8/2014 Hansen et al.

FOREIGN PATENT DOCUMENTS

DE 10353657 6/2005
WO WO 9842344 A1 * 10/1998 ........... A61K 9/0056
WO WO-2002/044159 6/2002
(Continued)

OTHER PUBLICATIONS

Ciammola et al., Aripiprazole in the treatment of Huntington's disease: a case series, Neuropsychiatric Disease and Treatment 2009:5, 1-4.*
Byrne et al., Beneficial effects of buspirone therapy in Huntington's disease, The American Journal of Psychiatry; Washington 151.7 (Jul. 1994): 1097.*
Roppongi et al, Perospirone in treatment of Huntington's disease: A first case report, Progress in Neuro-Psychypharmacology & Biological Psychiatry 31 (2007) 308-310.*
Hudkins et. al., Bioorganic and Medicinal Chemistry Letters, 8, pp. 1873-1876, (1998).*

(Continued)

Primary Examiner — Sventlana M Ivanova
(74) Attorney, Agent, or Firm — Julie K. Staple; Dinsmore & Shohl LLP

(57) ABSTRACT

The present invention relates to the use of 5-HT1 agonists in pharmaceutical compositions, compounds and methods for treatment of movement disorders related to neurological dysfunctions. The invention is particularly relevant for treatment of patients suffering from tardive dyskinesia, Parkinson's disease and associated disorders thereof. Kits of parts comprising the 5-HT1 agonist compounds or pharmaceutical compositions according to the present invention, as well as methods of preparation are also provided by the present invention.

11 Claims, 4 Drawing Sheets

(56) References Cited

FOREIGN PATENT DOCUMENTS

| WO | WO-2006/027681 | 3/2006 |
|---|---|---|
| WO | WO-2009/156380 | 12/2009 |
| WO | WO-2010/044736 | 4/2010 |
| WO | WO-2011/079313 | 6/2011 |
| WO | WO-2002/053139 | 7/2012 |
| WO | WO-2012163365 | 12/2012 |

OTHER PUBLICATIONS

Van Sickle et. al., Lipids, 27(3), pp. 157-160, (1992).*
Roos, Huntington's disease: a clinical review, Roos Orphanet Journal of Rare Diseases 2010, 5:40.*
Bonelli et al., A systematic review of the treatment studies in Huntington's disease since 1990, Expert Opinion on Pharmacotherapy, 8:2, 141-153.*
Kandel, Schwartz and Jessell, Principles of Neural Science, Fourth Ed., Chapter 43, The Basal Ganglia, pp. 853-867, 2000.*
Avital, A. et al., Zolmitriptan compared to propranolol in the treatment of acute neuroleptic-induced akathisia: A comparative double-blind study, European Neuropsychopharmacology, 19(7): 476-482, Jul. 1, 2009.
Bonifati, V. et al., Buspirone in levodopa-induced dyskinesias, Clin NeurPharmacol, 17(1): 73-82, 1994.
Carta et al., Dopamine released from 5-HT terminals is the cause of L-DOPA-induced dyskinesia in Parkinsonian rats, Brain, 130(7): 1819-1833, Jul. 1, 2007.
Dekundy, A. et al., Modulation of l-DOPA-induced abnormal involuntary movements by clinically tested compounds: Further validation of the rat dyskinesia model, Behavioural Brain Research, 179: 76-89, 2007.
Del Sorbo, F. et al., Levodopa-induced dyskinesias and their management, J Neurol, 255 Suppl 4: 32-41, 2008.
Elangbam, C. et al., 5-Hydroxytryptamine (5HT) Receptors in the Heart Valves of Cynomolgus Monkeys and Sprague-Dawley Rats, J Histochem Cytochem, 53(5):671-677, 2005.
Filip, M. et al., Overview on 5-HT receptors and their role in physiology and pathology of the central nervous system, Pharmacol. Reports. 61, 761-777, 2009.
Fox, S. et al., Serotonin and Parkinson's Disease: On Movement, Mood, and Madness, Movement Disorders, 24(9): 1255-66, 2009.
Grégoire, L. et al., Low doses of sarizotan reduce dyskinesias and maintain antiparkinsonian efficacy of L-Dopa in parkinsonian monkeys, Parkinsonism Relat Disord., 5(6): 445-52, 2009.
Jackson, M. et al., Effect of 5-HT1B/D receptor agonist and antagonist administration on motor function in haloperidol and MPTP-treated common marmosets, Pharmacology Biochemistry and Behavior, 79(3): 391-400, Nov. 1, 2004.
Jenner, P., Molecular mechanisms of L-DOPA-induced dyskinesia, Nat Rev Neurosci., 9(9): 665-77, 2008.
Kirik, D. et al., Growth and Functional Efficacy of Intrastriatal Nigral Transplants Depend on the Extent of Nigrostriatal Degeneration, J. Neurosci, 21: 2889-96, 2001.
Ludwig, C. et al., Buspirone, Parkinson's Disease, and the locus ceruleus, Clin Neuropharmacol., 9(4):373-8, 1986.
Moss, L. et al., Buspirone in the treatment of tardive dyskinesia, J Clin Psychopharmacol., 13(3): 204-9, Jun. 1993.
Muñoz, A. et al., Serotonin neuron-dependent and -independent reduction of dyskinesia by 5-HT1A and 5-HT1B receptor agonists in the rat Parkinson model, Experimental Neurology, 219: 298-307, 2009.
Muñoz, A. et al., Combined 5-HT1A and 5-HT1B receptor agonists for the treatment of L-DOPA-induced dyskinesia, Brain: A journal of Neurology, 131(12): 3380-94, Dec. 2008.
Newman-Tancredi, A., The importance of 5-HT1A receptor agonism in antipsychotic drug action: Rationale and perspectives, Current Opinion in investigational Drugs, 11(7): 802-812, 2010.
Ohno, Y., New Insight into the Therapeutic Role of 5-HT1A Receptors in Central Nervous System Disorders, Central Nervous System Agents in Medicinal Chemisty, 10: 148-157, 2010.
Olsson, M. et al., Forelimb Akinesia in the Rat Parkinson Model: Differential Effects of Dopamine Agonists and Nigral Transplants as Assessed by a New Stepping Test, J Neurosci, 15:3863-75, 1995.
Roppongi, T. et al., Perospirone in treatment of Huntington's disease: A first case report, Prog Neuropsychopharmacol Biol Psychiatry, 31(1):308-10, 2007.
Schallert, T. et al., A Clinically Relevant Unilateral Rat Model of Parkinsonian Akinesia, J. Neural TransplPlast, 3:332-3, 1992.
Tomiyama M. et al., A serotonin 5-HT1A receptor agonist prevents behavioral sensitization to L-DOPA in a rodent model of Parkinson's disease, Neuroscience Research, 52(2): 185-194, Jun. 1, 2005.
Gerlach, M. et al. Anti-dyskinetic effects of flibanserin on levodopa-induced dyskinesia in the 6-hydroxydopamine-lesioned rat model of Parkinson's disease. Poster presentations P2.111, Parkinsonism and Related Disorders 15S2 (2009) S29-S199.
Tfelt-Hansen., Does sumatriptan cross the blood-brain barrier in animals and man? J Headache Pain (2010) 11:5-12.
Kalvass et al., Use of plasma and brain unbound fractions to assess the extent of brain distribution of 34 drugs: Comparison of unbound concentration ratios to in vivo P-Glycoprotein efflux ratios. Drug metabolism and distribution, 35:660-666, 2007.
Uchiyama et al., Urinary dysfunction in early and untreated Parkinson's disease. J Neural Neurosurg Psychiatry. 2011; 82(12): 1382-6).
Wall et al., Distribution of Zolmitriptan into the CNS in healthy volunteers. Drugs R D 2005; 6 (3): 139-147.
Bara-Jimenez et al., Effects of serotonin 5-HT1A agonist in advanced Parkinson's disease. Movement Disorders vol. 20, No. 8, 2005, pp. 932-936.
Goetz et al., Sarotozan as a treatment for dyskinesias in Parkinson's disease: A double-blind placebo-controlled trial. Movement Disorders vol. 22, No. 2, 2007, pp. 179-186.
Rádl et al., Synthesis and analgesic activity of some deaza derivatives of anpirtoline. Arch. Pharm. Med. Chem. 332, 13-18 (1999).
Blackburn, T., Serotonergic agents and Parkinson's disease, Drug Discovery Today: Therapeutic Strategies, 1(1): 35-41, Sep. 2004.
A concise explanation of the relevance of DE-10353657.
Hasegawa et al., Japanese Journal of Medicine and Pharmaceutical Science, 57(3): 313-317, 2007.
Martin, G. et al., Receptor specificity and trigemino-vascular inhibitory actions of a novel 5-HT 1B/1D receptor partial agonist, 311C90 (zolmitriptan), British Journal of Pharmacology, 121: 157-164, 1997.
Concise Explanation of Relevance for Hasegawa et al., Japanese Journal of Medicine and Pharmaceutical Science, 57(3): 313-317, 2007.
Huang. X, et al., Role of tandospirone, a 5-HT1A receptor partial agonist, in the treatment of central nervous system disorders and the underlying mechanisms, Oncotarget, 8(60): 102705-102720, 2017.
Ishibashi, T. et al., Antiparkinsonian actions of a selective 5-HT1A agonist, tandospirone, in rats, Biogenic Amines, 18(3-6): 329-338, 2004.

* cited by examiner

COMBINATIONS OF SEROTONIN RECEPTOR AGONISTS FOR TREATMENT OF MOVEMENT DISORDERS

REFERENCE TO RELATED APPLICATIONS

This application is a continuation of U.S. patent application Ser. No. 13/879,128, now U.S. Pat. No. 9,186,359, which is the U.S. national stage of PCT/DK2011/050383, filed Oct. 13, 2011, which claims priority of U.S. Provisional Application Nos. 61/393,545, filed Oct. 15, 2010 and 61/491,945 filed Jun. 1, 2011, and Danish Patent Application No. PA201070441, filed Oct. 15, 2010. The entire content of each application is incorporated herein by reference.

FIELD OF THE INVENTION

The present invention relates to use of 5-HT1 agonists as compounds, in pharmaceutical compositions, and in methods for treatment of movement disorders related to neurological dysfunctions. The invention relates in particular to treatment of patients suffering from movement disorders related to impaired dopamine levels in the neuronal synapse, such as tardive dyskinesia, Parkinson's disease and associated disorders thereof. Kits of parts comprising the compounds or pharmaceutical compositions according to the present invention, as well as methods of preparation are also provided by the invention.

BACKGROUND OF THE INVENTION

Movement disorders are a group of diseases that affect the ability to produce and control body movement, and are often associated with neurological disorders or conditions associated with neurological dysfunction. Movement disorders may manifest themselves in abnormal fluency or speed of movement, excessive or involuntary movement, or slowed or absent voluntary movement. Akathisia for example, is a movement disorder characterized by unpleasant sensations of "inner" restlessness, mental unease, or dysphoria that results in inability of a patient to sit still or remain motionless. Patients typically have restless movement, including rocking from foot to foot and walking on the spot when standing, shuffling and tramping the legs, rocking back and forth, or swinging one leg on the other when sitting. In severe cases, patients constantly pace up and down in an attempt to relieve the sense of unrest, since the restlessness is felt from wakeup in the morning to sleep at night. Some patients have described the feeling as a sense of inner tension and torment or chemical torture.

Another example of a movement disorder is dyskinesia which characterized by various involuntary movements, which can affect discrete body parts or can become generalized and severely disabling. Tardive dyskinesia is one example of dyskinesia which is characterized by repetitive, involuntary, purposeless movements, such as grimacing, tongue protrusion, lip smacking, puckering and pursing of the lips, and rapid eye blinking. Involuntary movements of the fingers may appear as though the patient is playing an invisible guitar or piano.

Often, the neurological disorder or condition which causes the movement disorder is associated with dysfunction of the basal ganglia. The dysfunction may be idiopathic, induced by certain drugs or infections, or caused by genetic defects.

Parkinson's disease (PD) is an example of a neurological disorder associated with dysfunction of the basal ganglia. PD results in movement disorders and is characterized by muscle rigidity, tremor, postural abnormalities, gait abnormalities, a slowing of physical movement (bradykinesia) and in extreme cases a loss of physical movement (akinesia). The disease is caused by progressive death and degeneration of dopamine (DA) neurons in substantia nigra pars *compacta* and a dysfunctional regulation of dopamine neurotransmission. In order to replace the lost dopamine, PD is currently treated with Levodopa (L-DOPA, a precursor of dopamine), with dopamine agonists or other agents that act by increasing the concentration of dopamine in the synaptic cleft. PD is a common disease and affects 1% of persons above 60 years of age.

Unfortunately, the treatment of PD with L-DOPA often gives rise to dyskinesia (diminished voluntary movements and presence of involuntary movements) in advanced PD patients with impaired regulations of DA levels. This specific type of dyskinesia is called L-DOPA Induced Dyskinesia (LID) and is caused by excessive dopamine levels in the synapses (Jenner: *Nat Rev Neurosci*. 2008; 9(9): 665-77; Del Sorbo and Albanese: *J. Neurol*. 2008; 255 Suppl 4: 32-41). About 50% of patients treated with L-DOPA develop LID, which severely limits optimal treatment and reduce quality of life.

Movement disorders induced by drug therapy can also be related to treatment of other neurological or psychiatric diseases. Examples of these are tardive dyskinesia and akathesia, which are commonly developed as a side effect of long term treatment with neuroleptics for instance in patients suffering from e.g. schizophrenia.

Tardive dyskinesia may persist after withdrawal of the drug for months, years or can even be permanent. The primary prevention of tardive dyskinesia is achieved by using the lowest effective dose of a neuroleptic for the shortest time. If tardive dyskinesia is diagnosed, the therapy with the causative drug is discontinued. Both of these approaches cause difficulties for the therapeutical use of neuroleptics.

Shortly after the introduction of antipsychotic drugs in the 1950's, akathisia was recognized as one of the most common and distressing early onset adverse effects. Estimates of the prevalence of akathisia in neuroleptic-treated people range between 20% and 75%, occurring more frequently in the first three months of treatment. Akathisia is not only related to acute administration of a neuroleptic, but also to a rapid dosage increase. Unfortunately, akathisia may be difficult to distinguish from psychotic agitation or anxiety, especially if the person describes a subjective experience of akathisia in terms of being controlled by an outside force. Therefore, the dosage of the drug which causes the movement disorder may even be further increased after symptoms of akathisia.

Movement disorders are frequently caused by impaired regulation of dopamine neurotransmission. Dopamine acts by binding to synaptic dopamine receptors D1, D2, D4, and D5, and the binding is controlled by regulated release and re-uptake of dopamine. Impaired regulation of dopamine release or up-take can result in excess dopamine in the synapses, which lead to the development of movement disorders.

As mentioned above, PD is an example of a movement disorder associated with dysfunctional regulation of dopamine neurotransmission, which is caused by progressive degeneration of dopamine neurons. Tardive dyskinesia is another example of a movement disorder associated with dysfunctional regulation of dopamine neurotransmission. Neuroleptics act primarily on the dopamine system and are drugs which block D2 dopamine receptors, to prevent conditions associated with increased dopamine levels. Tardive dyskinesia has been suggested to result primarily from neuroleptic-induced dopamine super sensitivity in the nigrostriatal pathway, with the D2 dopamine receptor being most affected. Older neuroleptics, which have greater affinity for the D2 binding site, are associated with higher risks for tardive dyskinesia.

Dopamine release and re-uptake is regulated by a number of neurotransmitters, including serotonin (5-HT). Other neurotransmitters that directly or indirectly regulate dopamine neurotransmission are the inhibitory neurotransmitter gamma aminobutyric acid (GABA) and excitatory amino acid glutamate.

Serotonin acts by binding to different serotonergic receptors. These include the 5-HT1A, 5-HT1B, 5-HT1D, 5-HT1E, 5-HT1F, 5-HT2A, 5-HT2B, 5-HT2C, 5-HT3, 5-HT4, 5-HT5, 5-HT6, and 5-HT7 for which both agonists and antagonists have been found. The serotonin receptors 5-HT1A, 5-HT1B, 5-HT1D, 5-HT1E, 5-HT1F are located both post-synaptically and pre-synaptically and on the cell body. Serotonin neurotransmission is regulated by these receptors and by re-uptake mechanisms (Filip et al. *Pharmacol. Reports*, 2009, 61, 761-777; Ohno, *Central Nervous System Agents in Medicinal Chemistry*, 2010, 10, 148-157).

Agonists and antagonists of some serotonergic receptors have been investigated for treatment of some movement disorders. Several serotonin 5-HT1A agonists have been shown to ameliorate extrapyramidal side effects (EPS) associated with treatment with neuroleptics and to improve cognition in patients suffering from schizophrenia. (Newman-Tancredi: Current Opinion in Investigational Drugs, 2010, 11(7):802-812).

Modulators of serotonin (5-HT) neurotransmission have been shown to ameliorate or prevent LID. One example thereof is sarizotan, which is a 5-HT1A agonist and a dopamine receptor antagonist (Grégoire et al: *Parkinsonism Relat Disord.* 2009; 15(6): 445-52). In a phase 2A study and in an open labeled study sarizotan reduced LID. However, in several large phase 2b studies no significant effects of sarizotan compared to placebo could be shown. The lack of effect is suggested to be due to lack of efficacy of the drug, or worsening of the Parkinson symptoms caused by the dopamine receptor antagonistic effects of the compound.

The effects of buspirone on Parkinson's disease have been studied in a small open study (Ludwig et al: Clin Neuropharmacol. 1986; 9(4):373-8). It was found that doses (10-60 mg/day), which are normally used to treat patients suffering from anxiety, did not have any effects on Parkinson's disease or dyskinesia. At higher doses (100 mg/day) it was observed that buspirone reduced dyskinesia but with a significant worsening of disability ratings. This showed that high doses of buspirone could worsen the akinesia associated with Parkinson's disease.

Methods to treat LID using other 5-HT1A agonists have also been suggested in US 2007/0249621. It has further been shown in a case study that perospirone, which is a 5-HT1A agonist, could reduce involuntary movement of a patient suffering from Huntington's disease. (Roppongi et al: Prog Neuropsychopharmacol Biol Psychiatry. 2007; 31(1):308-10).

Recently it has been shown that a combination of a 5-HT1A and a 5-HT1B agonist increased efficacy in reducing L-DOPA induced dyskinesia can be obtained in animal models (e.g. Muñoz et al: *Brain.* 2008; 131(Pt 12): 3380-94; Muñoz et al: *Experimental Neurology* 219 (2009) 298-307). 5-HT1B agonists have potential to reduce LID via several mechanisms. However, 5-HT1B receptors are found in the heart and it has been proposed that modulators of these receptors can be involved in development of valvular heart disease and other cardiac disorders associated with the use of modulators of serotonin receptors and serotonin reuptake (Elangbam et al: J Histochem Cytochem 53:671-677, 2005).

The combined 5-HT1A and 5-HT1B agonist eltoprazine [1-(2,3-dihydro-benzo[1,4]dioxin-5-yl)piperazine has also recently been suggested for treatment of LID (WO2009/156380). Eltoprazine is estimated to be equipotent in terms of activation of 5-HT1A and 5-HT1B receptors, and in addition has 5-HT2C antagonistic effects. The long term effects of the use of the compound for treatment are unknown.

However, 5-HT1A agonists given in high doses can lead to the development of serotonin syndrome or serotonin toxicity a form of poisoning. The syndrome or toxicity is caused by increased activation of the 5-HT1A and 5-HT2A receptors. Serotonin syndrome, by definition, is a group of symptoms presenting as mental changes, autonomic nervous system malfunction, and neuromuscular complaints. Patients may present with confusion, agitation, diarrhea, sweating, shivering, hypertension, fever, increased white blood cell count, incoordination, marked increase in reflexes, muscle jerks, tremor, extreme stiffness, seizures and even coma. The severity of changes ranges from mild to fatal. Because of the severity of serotonin syndrome, it is therefore important to maintain a low exposure of the 5-HT1A agonist.

SUMMARY OF THE INVENTION

The present invention relates to use of 5-HT1 agonists for the treatment of movement disorders. The combined activation of different serotonergic receptors can lead to a synergic effect which more effectively influences the dopamine levels in the synapse and lead to efficacious treatment of the movement disorders described herein. Additionally, since the combination of different 5-HT1 agonists provided by the present invention may allow for a reduction in dosage of the 5-HT1A agonist compared to known treatments, the present invention can prevent or reduce the risk of the development of serotonin syndrome and adverse effects of treatment with 5-HT1A agonists.

The pharmaceutical compositions of the present invention comprise a compound, wherein said compound is either an agonist of two or more of the serotonin receptors selected from the group of 5-HT1B,
5-HT1D, and
5-HT1F, receptors, or a selective agonist of the 5-HT1D receptor, or a selective agonist of the 5-HT1F receptor, or a pharmaceutically acceptable derivative thereof, and optionally further comprises a 5-HT1A agonist or a pharmaceutically acceptable derivative thereof, for treatment, prevention or alleviation of movement disorders.

Pharmaceutical compositions according to the present invention can comprise a combination of two or more compounds wherein at least one is a) an agonist of the 5-HT1A receptor, and at least one other compound b) which is selected from: an agonist of two or more of the group of 5-HT1B, 5-HT1D and 5-HT1F receptors, or a selective 5-HT1D receptor agonist, or a selective 5-HT1F receptor agonist.

Thus, the present invention can relate to efficacious treatment of movement disorders by using drugs that are agonists of the serotonin 5-HT1A receptor and drugs that are either agonists of several serotonin receptors including 5-HT1B, 5-HT1D, and 5-HT1F receptors, or selective 5-HT1D receptor agonists, or selective agonists of the 5-HT1F receptors.

According to the present invention, said compound can be a combined agonist of the 5-HT1B receptor and 5-HT1D receptor, or a selective agonist of the 5-HT1F receptor, or a combined agonist of the 5-HT1B receptor, the 5-HT1D receptor and the 5-HT1F receptor, or a pharmaceutically acceptable derivative of all agonist mentioned herein.

In another embodiment of the present invention, the compound is a combined agonist of two or more of the 5-HT1B, the 5-HT1D and the 5-HT1F receptors having higher affinity and/or receptor activation efficacy for the 5-HT1D receptor than for the 5-HT1B receptor, or having higher affinity and/or receptor activation efficacy for the 5-HT1D receptor than for the 5-HT1B and 5-HT1F receptors.

In a preferred embodiment of the present invention, the pharmaceutical composition comprises a compound selected from the group of sumatriptan, zolmitriptan, rizatriptan, naratriptan, almotriptan, frovatriptan and eletriptan or a derivative thereof.

In another embodiment of the present invention, the pharmaceutical composition comprises a compound selected from the group of COL-144 (LY573144), LY334370, LY344864, or a derivative thereof.

In one embodiment of the present invention, the pharmaceutical composition comprises a 5-HT1A agonist selected from the group of alnespirone, binospirone, buspirone, gepirone, ipsapirone, perospirone, tandospirone, befiradol, repinotan piclozotan, osemozotan, flesinoxan, flibanserin and sarizotan or a derivative thereof, wherein the 5-HT1A agonists buspirone and tandospirone or derivatives thereof are particularly preferred.

In one embodiment, the compound is a combined agonist of two or more of the 5-HT1B, the 5-HT1D and the 5-HT1F receptors, or a selective 5-HT1D agonist, or a selective 5-HT1F agonist and is administered in doses of 0.05-200 mg/day, preferably in the ranges of 0.5 to 60 mg/day and even more preferred in the range of 0.5 to 10 mg/day.

In a preferred embodiment of the present invention, the 5-HT1A agonist is administered in doses of 0.5 mg/day to 100 mg/day and the compound is a combined agonist of two or more of the 5-HT1B, the 5-HT1D and the 5-HT1F receptors, or a selective 5-HT1D agonist, or a selective 5-HT1F agonist and is administered in doses of 0.1 mg/day to 60 mg/day, even more preferably wherein 5-HT1A agonist is administered in doses of 0.5 mg/day to 30 mg/day and the compound is a combined agonist of two or more of the 5-HT1B, the 5-HT1D and the 5-HT1F receptors, or a selective 5-HT1D agonist, or a selective 5-HT1F agonist and is administered in doses of 0.5 mg/day to 10 mg/day.

The pharmaceutical composition according to the present invention may further comprise one or more second active ingredients.

Pharmaceutical compositions according to present invention may further comprise one or more agents selected from the group of agents increasing the dopamine concentration in the synaptic cleft, dopamine, L-DOPA or dopamine receptor agonists or a derivative thereof.

The movement disorders according to the present invention are associated with altered synaptic dopamine levels, such as for example disorders selected from the group of akathisia, tardive dyskinesia and dyskinesia associated with Parkinson's disease, and in particular L-DOPA induced dyskinesia.

The pharmaceutical compositions according to the present invention may be formulated for parenteral administration, or for enteral administration such as oral administration. They may further be formulated for crossing the blood-brain barrier.

The present invention further provides compounds which are combined 5-HT1B, 5-HT1D and/or a 5-HT1F agonist for treatment for treatment, prevention or alleviation of movement disorders.

Methods for treatment, prevention or alleviation of movement disorders comprising one or more steps of administration of an effective amount of a pharmaceutical composition or a compound as defined herein are also aspects of the present invention.

In a preferred embodiment, such methods may further comprise a step of simultaneous, sequential or separate administration of an effective amount of one or more second active ingredients, such as a 5-HT1A agonist.

5-HT1A agonists used in methods of the present invention may be selected from the group of alnespirone, binospirone, buspirone, gepirone, ipsapirone, perospirone, tandospirone, befiradol, repinotan, piclozotan, osemozotan, flesinoxan, flibanserin and sarizotan or a derivative thereof, wherein buspirone and tandospirone are preferred.

In one embodiment of a method for treatment of the present invention, the 5-HT1A agonist is administered in doses of 0.05 mg/day to 500 mg/day, wherein the doses of 0.5 mg/day to 100 mg/day are preferred, and the doses of 0.5 mg/day to 30 mg/day are even more preferred.

Methods according to the present invention may further comprise steps of administering one or more agents selected from the group of agents increasing the dopamine concentration in the synaptic cleft, dopamine, L-DOPA or dopamine receptor agonists or a derivative thereof.

The present invention further provides kits of parts comprising the pharmaceutical composition or compound as defined herein for treatment, prevention or alleviation of movement disorders by simultaneous, sequential or separate administration. Such kits may further comprise one or more second active ingredients, such as a 5-HT1A agonist for example selected from the group of alnespirone, binospirone, buspirone, gepirone, ipsapirone, perospirone, tandospirone, befiradol, repinotan piclozotan, osemozotan, flesinoxan, flibanserin and sarizotan or a derivative thereof (wherein buspirone and tandospirone or derivatives thereof are preferred), or an agent increasing the dopamine concentration in the synaptic cleft, dopamine, L-DOPA, dopamine receptor agonists or a derivative thereof.

The present invention further provides methods for preparation of a pharmaceutical composition as defined herein.

Definitions

An "autoreceptor" as referred to herein, is a receptor located on a pre-synaptic nerve cell and serves as a part of a feedback loop in signal transduction. It is sensitive to those neurotransmitters or hormones that are released by the neuron in whose membrane the autoreceptor sits, and functions to downregulate the release of neurotransmitters in the synapse.

The term "blood-brain barrier" refers to selective tight junctions between endothelial cells in CNS capillaries that restrict the passage of solutes into the cerebrospinal fluid (CSF).

The term "agonist" in the present context refers to a substance capable of binding to and activating a receptor. A 5-HT1A receptor agonist (5-HT1A agonist) is thus capable of binding to and activating the 5-HT1A receptor. A 5-HT1B receptor agonist (5-HT1B agonist) is capable of binding to and activating the 5-HT1B receptor. A 5-HT1D receptor agonist (5-HT1D agonist) is capable of binding to and activating the 5-HT1D receptor. A 5-HT1F receptor agonist (5-HT1F agonist) is capable of binding to and activating the 5-HT1F receptor. Said agonist compound may be an agonist of several different types of receptors, and thus capable of binding and activating several different types of receptors. Said agonist compound can also be a selective agonist which only binds and activates one type of receptor.

The term "antagonist" in the present context refers to a substance capable of inhibiting the effect of a receptor agonist.

The terms "dopamine," "DA" and "4-(2-aminoethyl)benzene-1,2-diol," refer to a catecholamine neurotransmitter and hormone. Dopamine is a precursor of adrenaline (epinephrine) and noradrenaline (norepinephrine) and activates the five types of dopamine receptors—D1, D2, D3, D4, and D5—and their variants.

A "heteroreceptor" as referred to herein, is a receptor regulating the synthesis and/or the release of mediators other than its own ligand. Heteroreceptors are presynaptic receptors that respond to neurotransmitters, neuromodulators, or neurohormones released from adjacent neurons or cells.

An "individual" in need as referred to herein, is an individual that may benefit from the administration of a compound or pharmaceutical composition according to the present invention. Such an individual may suffer from a movement disorder or be in risk of suffering from a movement disorder. The individual may be any human being, male or female, infant, middle-aged or old. The movement disorder to be treated or prevented in the individual may relate to the age of the individual, the general health of the individual, the medications used for treating the individual and whether or not the individual has a prior history of suffering from diseases or disorders that may have or have induced movement disorders in the individual.

"L-DOPA" or "3,4-dihydroxyphenylalanine" is a precursor to the neurotransmitters dopamine, norepinephrine (noradrenaline), and epinephrine (adrenaline). L-DOPA is able to cross the blood-brain barrier, and is converted to dopamine by the enzyme aromatic L-amino acid decarboxylase (AADC), also known as DOPA decarboxylase (DDC). L-DOPA is used for treatment of Parkinson's disease.

A "neurotransmitter" as referred to herein, is a substance, which transmits signals from a neuron to a target cell across a neuronal synapse.

The terms "Parkinson's disease," "Parkinson's" and "PD" refer to a neurological syndrome characterized by a dopamine deficiency, resulting from degenerative, vascular, or inflammatory changes in the basal ganglia of the substantia nigra. This term also refers to a syndrome which resembles Parkinson's disease, but which may or may not be caused by Parkinson's disease, such as Parkinsonian-like side effects caused by certain antipsychotic drugs. Parkinson's disease is also referred to as paralysis agitans and shaking palsy.

"Partial agonists" in the present context are compounds able to bind and activate a given receptor, but having only partial efficacy at the receptor relative to a full agonist. Partial agonists can act as antagonists when competing with a full agonist for receptor occupancy and producing a net decrease in the receptor activation compared to the effects or activation observed with the full agonist alone.

"Selective agonists" in the present context are compounds which are selective and therefore only binds and activates one type of receptor. Thus a selective 5-HT1D receptor agonist only is selective for the 5-HT1D receptor, and a selective 5-HT1F receptor agonist is selective for the 5-HT1F receptor.

The term "synapse" refers to an area of a neuron that permits said neuron to pass an electrical or chemical signal to another cell. In a synapse, a plasma membrane of the signal-passing neuron (the pre-synaptic neuron) comes into close apposition with the membrane of the target (post-synaptic) cell.

The term "pharmaceutically acceptable derivative" in present context includes pharmaceutically acceptable salts, which indicate a salt which is not harmful to the patient. Such salts include pharmaceutically acceptable basic or acid addition salts as well as pharmaceutically acceptable metal salts, ammonium salts and alkylated ammonium salts. A pharmaceutically acceptable derivative further includes esters and prodrugs, or other precursors of a compound which may be biologically metabolized into the active compound, or crystal forms of a compound.

The terms "serotonin," "5-hydroxytryptamine" and "5-HT" refers to a phenolic amine neurotransmitter produced from tryptophan by hydroxylation and decarboxylation in serotonergic neurons of the central nervous system and enterochromaffin cells of the gastrointestinal tract. Serotonin is a precursor of melatonin.

The term "terminal" in the present context refers to a neuronal terminal.

The term "therapeutically effective amount" of a compound as used herein refers to an amount sufficient to cure, alleviate, prevent, reduce the risk of, or partially arrest the clinical manifestations of a given disease or disorder and its complications. An amount adequate to accomplish this is defined as a "therapeutically effective amount".

The terms "treatment" and "treating" as used herein refer to the management and care of a patient for the purpose of combating a condition, disease or disorder. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The patient to be treated is preferably a mammal, in particular a human being. Treatment of animals, such as mice, rats, dogs, cats, cows, sheep and pigs, is, however, also within the scope of the present invention. The patients to be treated according to the present invention can be of various ages.

A "triptan" in the present context is a compound part of a family of tryptamine-based drugs used as abortive medication in the treatment of migraines and cluster headaches. The triptans are agonists of the serotonin 5-HT1B, 5-HT1D, 5-HT1E and/or 5-HT1F receptors, and may be or may not be selective agonists of one or more of the serotonin 5-HT1B, 5-HT1D, 5-HT1E and/or 5-HT1F receptors.

DETAILED DESCRIPTION OF THE INVENTION

Figure 1:
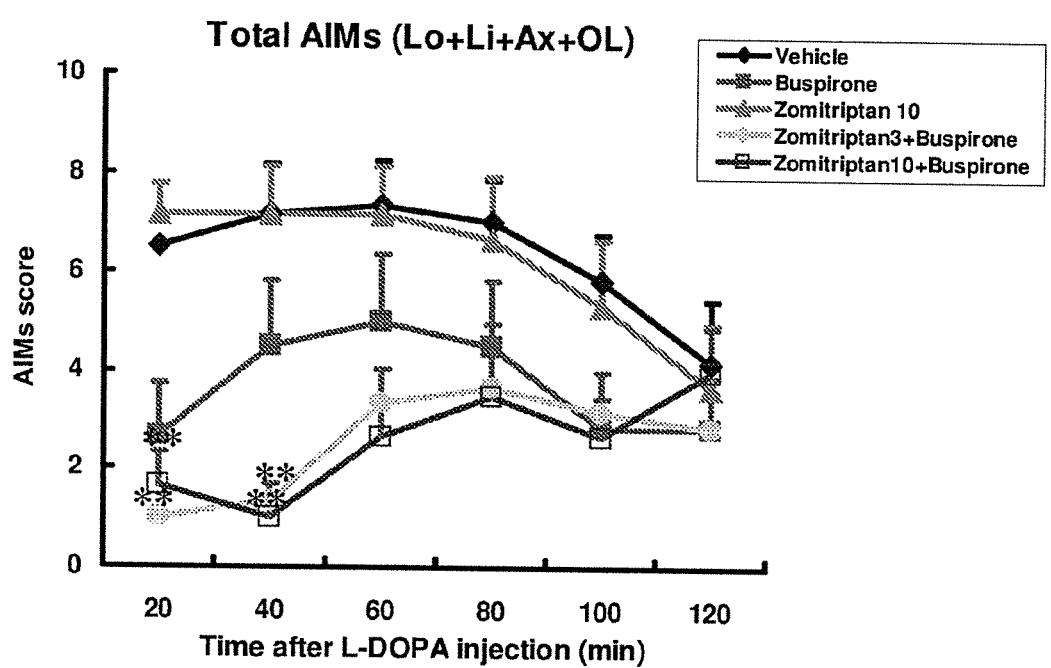
FIG. 1 shows the effect of combination of buspirone and zolmitriptan on L-DOPA induced abnormal involuntary movements (AIMs) in rats (Total AIMs=sum of locomotive (LO) or axial (AX), limb (LI), and orolingual (OL) AIM scores). Asterics (**) denote effects of P<0.01 compared with vehicle calculated by use of the one-way ANOVA test and the Tukey post-hoc test in each time point. Diamonds denote rats administered vehicle only, filled square denote rats administered 1 mg/kg/day buspirone, triangles denote rats administered 10 mg/kg/day zolmitriptan, filled circles denote rats administered 3 mg/kg/day zolmitriptan in combination with 1 mg/kg/day buspirone and open squares denote rats administered 10 mg/kg/day zolmitriptan in combination with 1 mg/kg/day buspirone. The results demonstrate that a combined use of buspirone (a 5-HT1A agonist) and zolmitriptan (a combined 5-HT1B/5-HT1D receptor agonist that has higher affinity and/or receptor activation efficacy of 5-HT1D receptors compared to 5-HT1B receptors) has potency to reduce AIM significantly compared to the use of buspirone or zolmitriptan alone.

The present invention relates to the use of combinations of compounds that are able to modulate dopamine neurotransmission through activations of serotonin receptors. More specifically the present invention relates to combinations of compounds that act as agonists of the serotonin 5-HT1A receptor and compounds that are agonists of several serotonin receptors including 5-HT1B, 5-HT1D, and 5-HT1F receptors.

5-HT1 Receptors

Serotonin, or 5-Hydroxytryptamine (5-HT), is a neurotransmitter that has important functions in the central nervous system of humans and animals. Serotonin has been found to regulate mood, appetite, sleep, muscle contraction, and some cognitive functions including memory and learning. Serotonin acts by binding to different serotonergic receptors, also known as 5-HT receptors. These are a group of G protein-coupled receptors (GPCRs) and ligand-gated ion channels (LGICs) found in the central and peripheral nervous systems. The 5-HT receptors include the 5-HT1A, 5-HT1B, 5-HT1D, 5-HT1E, 5-HT1F, 5-HT2A, 5-HT2B, 5-HT2C, 5-HT3, 5-HT4, 5-HT5, 5-HT6, and 5-HT7 receptors for which both agonists and antagonists have been found.

The 5-HT1 receptors is a subfamily of 5-HT receptors including the 5-HT1A, 5-HT1B, 5-HT1D, 5-HT1E, and 5-HT1F receptors, which are G protein-coupled receptors (GPCRs) that mediate inhibitory neurotransmission. These are located post-synaptically, pre-synaptically and on the cell body of the neurons in the cerebral cortex, hippocampus, septum, amygdale, raphe nuclei, basal ganglia and thalamus. Due to their inhibitory roles in neurotransmission, the 5-HT1 receptors play an important role in regulation of dopamine release.

5-HT1A receptors are widely distributed in the CNS. They are principally located in the hippocampus, cingulated end enthorhinal cortices, lateral septum and mesencephalic raphe nucleus. The 5-HT1A receptors are involved in motor behavior, copulatory behavior, pain perception, emotional behavior, and cognitive processes. The 5-HT1A receptors are autoreceptors in the raphe nuclei where they are located on the cell bodies or dendrites of 5-HT neurons, or they are post-synaptic receptors. In general, activation of 5-HT1A receptors reduces the release of neurotransmitters such as 5-HT and the excitatory amino acid glutamate, which further leads to changes in dopamine release.

The 5-HT1B receptor is highly expressed in the basal ganglia and the frontal cortex. They function as autoreceptors on the terminals of 5-HT neurons inhibiting 5-HT release, or as terminal heteroreceptors on gamma-amino butyric acid (GABA), acetylcholine (Ach) and glutamate neurons where they control the release of these neurotransmitters.

The 5-HT1D receptor is present both pre-synaptically and post-synaptically in the CNS and in the periphery. The highest expression of 5-HT1D receptors in the rat brain has been found in the basal ganglia (particularly in the substantia nigra, globus pallidus and caudate putamen), the hippocampus and the cortex, while in the human brain in the basal ganglia (the substantia nigra, globus pallidus), the midbrain (the periaqueductal grey) and the spinal cord. 5-HT1D receptors are either autoreceptors on the terminals of 5-HT neurons (they inhibit 5-HT release) or terminal heteroreceptors on gamma amino butyric acid (GABA), acetylcholine (Ach) and glutamate neurons (they control the release of these neurotransmitters). 5-HT1D receptors have been described as being involved in pain perceptions and 5-HT1D agonists have been developed as treatment of migraine.

The 5-HT1F receptor has been found in several CNS areas (the dorsal raphe nucleus, hippocampus, cingulate and entorhinal cortices, claustrum, caudate nucleus, brainstem) and based on localization suggested to function as an autoreceptor. The triptans show high affinity for the 5-HT1F receptors.

The basal ganglia are a group of nuclei in the brain which are connected to cerebral cortex, thalamus and other brain areas. The basal ganglia are associated with a variety of functions, including motor control. The striatum is the largest part of the basal ganglia, and receives input from many part of the brain, but sends output only to other parts of the basal ganglia. The *pallidum* receives the most important input from the striatum, and sends inhibitory output to a number of motor-related areas of the cortex. The substantia nigra is an important part of the basal ganglia and is divided into to parts. The substantia nigra pars reticulate receives input from other areas of the brain, while the substantia nigra pars *compacta* provides dopamine into the striatum. Thus, the substantia nigra pars *compacta* plays an important role in dopamine neurotransmission and its most prominent function is motor control.

The 5-HT1 receptors are particularly important in the regulation of PD and associated movement disorders. In progressed PD there is extensive degenerative loss of DA neurons in substantia nigra. Transformation of L-DOPA to dopamine takes place in the remaining dopamine neurons and in 5-HT (serotonin) neurons, which have been shown to be able to metabolize L-DOPA to dopamine and store and release dopamine. However, serotonin neurons lack a pre-synaptic feedback control mechanism for the release of dopamine, such as the dopamine transporter and D2 autoreceptor and are therefore unable to regulate release of dopamine in a normal way. This leads to impaired levels of DA in the synapse and to movement disorders 5-HT1 Agonists The present invention relates to a combination of 5-HT1 agonist for treatment of movement disorders, for example such as movement disorders associated with altered or impaired DA regulation.

The combined effects of an 5-HT1A agonist and either a) an agonist of two or more of the 5-HT1B, 5-HT1D, and 5-HT1F receptors or b) a selective 5-HT1D receptor agonist, or c) a selective agonist of a 5-HT1F receptor lead to an effective suppression of the excessive DA neurotransmission, that ameliorates or treats movement disorders such as for example LID.

The present invention relates to compounds which are either a) agonists of two or more of the group of serotonin
  5-HT1B,
  5-HT1D,
  5-HT1F
receptors (a combined agonist), or b) a selective 5-HT1D agonist, or c) selective agonists of the 5-HT1F receptor, or pharmaceutically acceptable derivative thereof. Such agonists may be compounds binding and activating the 5-HT1B receptor and the 5-HT1D receptor, thus combined 5-HT1B receptor and 5-HT1D receptor agonists. Such agonists may further be compounds binding and activating the 5-HT1F receptor, thus agonists of the 5-HT1F receptor, or the agonists may further be compounds binding and activating the 5-HT1D receptor, such as selective 5-HT1D receptor agonists. Such agonists may additionally be compounds binding and activating the 5-HT1B receptor, 5-HT1D receptor and the 5-HT1F receptor, thus a combined agonist of the 5-HT1B, 5-HT1D and 5-HT1F receptors. Pharmaceutically acceptable derivatives of combined 5-HT1B and 5-HT1D agonists, and/or 5-HT1F agonist are also part of the present invention.

In one embodiment, of the present invention, the 5-HT1 agonist of the present invention is a compound which is a combined agonist of the two or more of the serotonin receptors
  5-HT1A,
  5-HT1B,
  5-HT1D
  5-HT1F Such an agonists may be compounds binding and activating the 5-HT1A receptor and the 5-HT1B receptor, or compounds binding and activating the 5-HT1A receptor and the 5-HT1D receptor, or compounds binding and activating the 5-HT1A receptor and the 5-HT1F receptor, or compounds binding and activating the 5-HT1A receptor and the 5-HT1B receptor and the 5-HT1D receptor, or compounds binding and activating the 5-HT1A receptor and the 5-HT1B receptor and the 5-HT1F receptor, or compounds binding and activating the 5-HT1A receptor and the 5-HT1D receptor and the 5-HT1F receptor, or compounds binding and activating the 5-HT1A, 5-HT1B, 5-HT1D and the 5-HT1F receptors.

Certain mixed 5-HT1B/5-HT1D receptor agonists have been developed, and a subgroup of 5-HT1B/5-HT1D receptor agonists are collectively called "the triptans". The triptans have been developed as medication for treatment of migraine and have been used for therapy for more than a decade. These compounds include sumatriptan, zolmitriptan, rizatripan, naratripan, almotriptan, frovatriptan and eletriptan. In addition to their effects on 5-HT1B and 5-HT1D receptors, some "triptans" bind to and activate 5-HT1F receptors and other 5-HT receptors.

The combined agonist of two or more of the 5-HT1B, 5-HT1D and 5-HT1F receptors according to the present invention may be selected from the group of sumatriptan (1-[3-(2-dimethylaminoethyl)-1H-indol-5-yl]-N-methyl-methanesulfonamide), zolmitriptan ((S)-4-([3-[2-(dimethyl-amino)ethyl]-1H-indol-5-yl]methyl)-1,3-oxazolidin-2-one), rizatripan (N,N-dimethyl-2-[5-(1H-1,2,4-triazol-1-ylm-ethyl)-1H-indol-3-yl]ethanamine), naratripan (N-methyl-2-[3-(1-methylpiperidin-4-yl)-1H-indol-5-yl]ethanesulfona-mide), almotriptan (N,N-dimethyl-2-[5-(pyrrolidin-1-ylsulfonylmethyl)-1H-indol-3-yl]-ethanamine), frovatriptan ((+)-(R)-3-methylamino-6-carboxamido-1,2,3,4-tetrahydro-carbazole) and eletriptan ((R)-3-[(−1-methylpyrrolidin-2-yl) methyl]-5-(2-phenyl sulfonylethyl)-1H-indole) or a pharmaceutically acceptable derivative thereof.

In a preferred embodiment the combined agonist of two or more of the 5-HT1B, 5-HT1D and 5-HT1F receptors are selected from rizatriptan, naratriptan, zolmitriptan and frovatriptan or a pharmaceutically acceptable derivative thereof.

In a preferred embodiment of the present invention, the combined agonist of two or more of the 5-HT1B, 5-HT1D and 5-HT1F receptors are selected from zolmitriptan and frovatriptan or a pharmaceutically acceptable derivative thereof.

Compounds according to the present invention which are capable of binding and activating several 5-HT receptors, can have different affinities and/or different receptor activation efficacy for different 5-HT1 receptors, wherein affinity refers to the number and size of intermolecular forces between a ligand and its receptor, and residence time of a ligand at its receptor binding site, and receptor activation efficacy refers to the ability of the compound to produce a biological response upon binding to the target receptor and the quantitative magnitude of this response. Such differences in affinity and receptor activation efficacy can be determined by receptor binding/activation studies which are conventional in the art, for instance by generating $EC_{50}$ and Emax values for stimulation of [$^{35}$S]-GTPγS binding in cells expressing one or several types of 5-HT1 receptors as mentioned herein, or on tissues expressing the different types of 5-HT receptors. High affinity means that a lower concentration of a compound is needed to obtain a binding of 50% of the receptors compared to compounds which have lower affinity; high receptor activation efficacy means that a lower concentration of the compound is needed to obtain a 50% receptor activation response (low $EC_{50}$ value), compared to compounds which have lower affinity and/or receptor activity efficacy (higher $EC_{50}$ value).

The property of differing affinity and/or receptor activation efficacy for 5-HT1 receptors can be used for treatment, since the responses of different receptors are modified when the administered doses of the compound are varied. In one embodiment of the present invention, the compounds which are combined agonists of the present invention have differing affinities and/or receptor activation efficacies for two or more of the receptors selected from 5-HT1B, 5-HT1D and 5-HT1F serotonin receptors. In another embodiment the compounds which are combined agonists of the present invention have different affinities and/or receptor activation efficacies for two or more of the receptors selected from 5-HT1A, 5-HT1B, 5-HT1D and 5-HT1F serotonin receptors. Thus, in one embodiment of the present invention, a compound which is a combined agonist of the 5-HT1B, 5-HT1D and 5-HT1F receptors has higher affinity and/or receptor activation efficacy for the 5-HT1B receptor compared to the 5-HT1D and 5-HT1F receptors, or a compound which is a combined agonist of the 5-HT1B, 5-HT1D and 5-HT1F receptors has higher affinity and/or receptor activation efficacy for the 5-HT1D receptor compared to the 5-HT1B and 5-HT1F receptors, or a compound which is a combined agonist of the 5-HT1B, 5-HT1D and 5-HT1F receptors has higher affinity and/or receptor activation efficacy for the 5-HT1F receptor compared to the 5-HT1B and 5-HT1D receptors.

In one embodiment of the present invention, the compound which is a combined agonist of the 5-HT1B, 5-HT1D and 5-HT1F receptor has an $EC_{50}$ value for the 5-HT1D receptor which is less than the $EC_{50}$ value for the 5-HT1B receptor, such as in the range of 0-99% of the $EC_{50}$ value for the 5-HT1B receptor, for example less than 99% such as less than 85%, such as less than 70% such as less than 60%, such as less than 50%, such as less than 40%, such as less than 30%, such as less than 20% such as less than 1%, such as less than 0.01% of the $EC_{50}$ value for the 5-HT1B receptor or less.

The receptor activation potency of compounds which are 5-HT1 receptor agonists of the present invention can also be measured in $p(A_{50})$ values which is a conventional method for determining the receptor activation efficacy of an agonist. In another embodiment of the present invention, the compound which is a combined agonist of the 5-HT1B, 5-HT1D and/or the 5-HT1F receptor compounds can have difference in $p(A_{50})$ value for the different receptors. For instance such a difference can be in the range of 1 to 5, such as 1 to 2, or such as 2 to 3 or such as 3 to 4, or such as 4 to 5 or more.

In a preferred embodiment of the present invention, the difference between the $p(A_{50})$ of the 5-HT1D receptor and the $p(A_{50})$ of the 5-HT1B is in the range of 1 to 5.

Compounds which have higher receptor activation efficacy for the 5-HT1D receptor than for the 5-HT1B receptor or the 5-HT1F receptors are preferred according to the present invention. Thus in a preferred embodiment of the present invention, the compound is zolmitriptan, eletriptan and rizatripan or a pharmaceutically acceptable derivative thereof.

Pharmaceutical compositions as defined herein can comprise a selective 5-HT1D receptor agonist or a pharmaceutically acceptable derivative thereof and may optionally further comprise a 5-HT1A receptor agonist.

In one embodiment of the present invention, the 5-HT1F receptors agonist is selected from the group of COL-144 (lasmiditan), LY573144: 2,4,6-trifluoro-N-[6-[(1-methylpiperidin-4-yl)carbonyl]pyridin-2yl]benzamide)), LY334370 (4-fluoro-N-[3-(1-methylpiperidin-4-yl)-1H-indol-5-yl]benzamide) and LY344864 (N-(6-dimethylamino-6,7,8,9-tetrahydro-5H-carbazol-3-yl)-4-fluorobenzamide) or a pharmaceutically acceptable derivative thereof.

The present invention further relates to agonists of the serotonin 5-HT1A receptor (5-HT1A agonists). Such 5-HT1A agonists may be partial or may not be partial agonists of the 5-HT1A receptor. The 5-HT1A agonists may be selected from the group consisting of alnespirone ((+)-4-dihydro-2H-chromen-3-yl]-propylamino]butyl]-8-azaspiro[4.5]decane-7,9-dione), binospirone (8-[2-(2,3-dihydro-1,4-benzodioxin-2-ylmethylamino)ethyl]-8-azaspiro [4.5]decane-7,9-dione), buspirone (8-[4-(4-pyrimidin-2-ylpiperazin-1-yl)butyl]-8-azaspiro[4.5]decane-7,9-dione), gepirone (4,4-dimethyl-1-[4-(4-pyrimidin-2-ylpiperazin-1-yl)butyl]piperidine-2,6-dione), ipsapirone (9,9-dioxo-8-[4-(4-pyrimidin-2-ylpiperazin-1-yl)butyl]-9λ6-thia-8-azabicyclo[4.3.0]nona-1,3,5-trien-7-one), perospirone (3 aR,7aS)-2-{4-[4-(1,2-benzisothiazol-3-yl)piperazin-1-yl] butyl}hexahydro-1H-isoindole-1,3(2H)-dione, tandospirone ((1R,2R,6S,7S)-4-{4-[4-(pyrimidin-2-yl)piperazin-1-yl]butyl-4-azatricyclo[5.2.1.02,6]decane-3,5-dione), befiradol (F-13,640) (3-chloro-4-fluorophenyl-[4-fluoro-4-([(5-methylpyridin-2-yl)methylamino]-methyl)piperidin-1-yl]methanone, repinotan ((R)-(−)-2-[4-[(chroman-2-ylmethyl)-amino]-butyl]-1,1-dioxo-benzo[d]isothiazolone), piclozotan (3-chloro-4-[4-[4-(2-pyridinyl)-1,2,3,6-tetrahydropyridin-1-yl]butyl]-1,4-benzoxazepin-5(4H)-one), osemozotan (5-(3-[((2S)-1,4-benzodioxan-2-ylmethyl)amino]propoxy)-1,3-benzodioxole), flesinoxan (4-fluoro-N-[2-[4-[(3 S)-3-(hydroxymethyl)-2,3-dihydro-1,4-benzodioxin-8-yl] piperazin-1-yl]ethyl]benzamide), flibanserin (1-(2-{4-[3-(trifluoromethyl)phenyl]piperazin-1-yl}ethyl)-1,3-dihydro-2H-benzimidazol-2-one), sarizotan (EMD-128,130) (1-[(2R)-3,4-dihydro-2H-chromen-2-yl]-N-([5-(4-fluorophenyl)pyridin-3-yl]-methyl)methanamine) or a pharmaceutically acceptable derivative thereof.

In one embodiment of the present invention, the 5-HT1A agonist is a partial agonist of the 5-HT1A receptor.

In a preferred embodiment of the present invention, the 5-HT1A agonist is buspirone, tandospirone or gepirone or a pharmaceutically acceptable derivative thereof.

In an even more preferred embodiment of the present invention, the 5-HT1A agonist is buspirone or tandospirone or a pharmaceutically acceptable derivative thereof.

According to the present invention, a combined 5-HT1B and 5-HT1D receptor agonist or a pharmaceutically acceptable derivative thereof, may be used in combination with a 5-HT1A receptor agonist or a pharmaceutically acceptable derivative thereof. Thus according to the present invention, sumatriptan is used in combination with alnespirone, or sumatriptan is used in combination with binospirone, or sumatriptan is used in combination with buspirone, or sumatriptan is used in combination with gepirone, or sumatriptan is used in combination with ipsapirone, or sumatriptan is used in combination with perospirone, or sumatriptan is used in combination with tandospirone, or sumatriptan is used in combination with befiradol, or sumatriptan is used in combination with repinotan, or sumatriptan is used in combination with piclozotan, or sumatriptan is used in combination with osemozotan, or sumatriptan is used in combination with flesinoxan, or sumatriptan is used in combination with flibanserin, or sumatriptan is used in combination with sarizotan, or zolmitriptan is used in combination with alnespirone, or zolmitriptan is used in combination with binospirone, or zolmitriptan is used in combination with buspirone, or zolmitriptan is used in combination with gepirone, or zolmitriptan is used in combination with ipsapirone, or zolmitriptan is used in combination with, or zolmitriptan is used in combination with perospirone, or zolmitriptan is used in combination with tandospirone, or zolmitriptan is used in combination with befiradol, or zolmitriptan is used in combination with repinotan, or zolmitriptan is used in combination with piclozotan, or zolmitriptan is used in combination with osemozotan, or zolmitriptan is used in combination with flesinoxan, or zolmitriptan is used in combination with flibanserin, or zolmitriptan is used in combination with sarizotan, or rizatripan is used in combination with alnespirone, or rizatripan is used in combination with binospirone, or rizatripan is used in combination with buspirone, or rizatripan is used in combination with gepirone, or rizatripan is used in combination with ipsapirone, or rizatripan is used in combination with perospirone, or rizatripan is used in combination with tandospirone, or rizatripan is used in combination with befiradol, or rizatripan is used in combination with repinotan, or rizatripan is used in combination with piclozotan, or rizatripan is used in combination with osemozotan, or rizatripan is used in combination with flesinoxan, or rizatripan is used in combination with flibanserin, or rizatripan is used in combination with sarizotan, or naratripan is used in combination with alnespirone, or naratripan is used in combination with binospirone, or naratripan is used in combination with buspirone, or naratripan is used in combination with gepirone, or naratripan is used in combination with ipsapirone, or naratripan is used in combination with perospirone, or naratripan is used in combination with tandospirone, or naratripan is used in combination with befiradol, or naratripan is used in combination with repinotan, or naratripan is used in combination with piclozotan, or naratripan is used in combination with osemozotan, or naratripan is used in combination with flesinoxan, or naratripan is used in combination with flibanserin, or naratripan is used in combination with sarizotan, or almotriptan is used in combination with alnespirone, or almotriptan is used in combination with binospirone, or almotriptan is used in combination with buspirone, or almotriptan is used in combination with gepirone, or almotriptan is used in combination with ipsapirone, or almotriptan is used in combination with perospirone, or almotriptan is used in combination with tandospirone, or almotriptan is used in combination with befiradol, or almotriptan is used in combination with repinotan, or almotriptan is used in combination with piclozotan, or almotriptan is used in combination with osemozotan, or almotriptan is used in combination with flesinoxan, or almotriptan is used in combination with flibanserin, or almotriptan is used in combination with sarizotan, or frovatriptan is used in combination with alnespirone, or frovatriptan is used in combination with binospirone, or frovatriptan is used in combination with buspirone, or frovatriptan is used in combination with gepirone, or frovatriptan is used in combination with ipsapirone, or frovatriptan is used in combination with perospirone, or frovatriptan is used in combination with tandospirone, or frovatriptan is used in combination with befiradol, or frovatriptan is used in combination with repinotan, or frovatriptan is used in combination with piclozotan, or frovatriptan is used in combination with osemozotan, or frovatriptan is used in combination with flesinoxan, or frovatriptan is used in combination with flibanserin, or frovatriptan is used in combination with sarizotan, or eletriptan is used in combination with alnespirone, or eletriptan is used in combination with binospirone, or eletriptan is used in combination with buspirone, or eletriptan is used in combination with gepirone, or eletriptan is used in combination with ipsapirone, or eletriptan is used in combination with perospirone, or eletriptan is used in combination with tandospirone, or eletriptan is used in combination with befiradol, or eletriptan is used in combination with repinotan, or eletriptan is used in combination with piclozotan, or eletriptan is used in combination with osemozotan, or is used in combination with flesinoxan, or eletriptan is used in combination with flibanserin, or eletriptan is used in combination with sarizotan.

In a more preferred embodiment of the present invention, the combined 5-HT1B and 5-HT1D receptor agonist is selected from the group of zolmitriptan and frovatriptan, or a pharmaceutically acceptable derivative thereof and the 5-HT1A receptor agonist is selected from buspirone, tandospirone or gepirone or a pharmaceutically acceptable derivative thereof. Even more preferably the combined 5-HT1B and 5-HT1D receptor agonist compound is zolmitriptan or a pharmaceutically acceptable derivative thereof and the 5-HT1A receptor agonist is buspirone or a pharmaceutically acceptable derivative thereof.

According to the present invention, a 5-HT1F receptor agonist or a pharmaceutically acceptable derivative thereof may be used in combination with a 5-HT1A receptor agonist. Such 5-HT1F receptor agonists may be selected from the group of COL-144 (also called LY573144 or lasmiditan), LY334370, or LY344864.

According to the present invention, a 5-HT1F receptor agonist or a pharmaceutically acceptable derivative thereof may be used in combination with a 5-HT1A receptor agonist or a pharmaceutically acceptable derivative thereof. Thus according to the present invention, COL-144 is used in combination with alnespirone, or COL-144 (lasmiditan) is used in combination with alnespirone, or COL-144 (lasmiditan) is used in combination with binospirone, or COL-144 is used in combination with buspirone, or COL-144 is used in combination with gepirone, or COL-144 is used in combination with ipsapirone, or COL-144 is used in combination with perospirone, or COL-144 is used in combination with tandospirone, or COL-144 is used in combination with befiradol, or COL-144 is used in combination with repinotan, or COL-144 is used in combination with piclozotan, or COL-144 is used in combination with osemozotan, or COL-144 is used in combination with flesinoxan, or COL-144 is used in combination with flibanserin, or COL-144 is used in combination with sarizotan, or LY573144 is used in combination with alnespirone, or LY573144 is used in combination with binospirone, or LY573144 is used in combination with buspirone, or LY573144 is used in combination with gepirone, or COL-144 is used in combination with ipsapirone, or LY573144 is used in combination with perospirone, or LY573144 is used in combination with tandospirone, or LY573144 is used in combination with befiradol, or LY573144 is used in combination with repinotan, or LY573144 is used in combination with piclozotan, or
LY573144 is used in combination with osemozotan, or
LY573144 is used in combination with flesinoxan, or
LY573144 is used in combination with flibanserin, or
LY573144 is used in combination with sarizotan, or
LY334370 is used in combination with alnespirone, or
LY334370 is used in combination with binospirone, or
LY334370 is used in combination with buspirone, or
LY334370 is used in combination with gepirone, or
LY334370 is used in combination with ipsapirone, or
LY334370 is used in combination with perospirone, or
LY334370 is used in combination with tandospirone, or
LY334370 is used in combination with befiradol, or
LY334370 is used in combination with repinotan, or
LY334370 is used in combination with piclozotan, or
LY334370 is used in combination with osemozotan, or
LY334370 is used in combination with flesinoxan, or
LY334370 is used in combination with flibanserin, or
LY334370 is used in combination with sarizotan, or
LY344864 is used in combination with alnespirone, or
LY344864 is used in combination with binospirone, or
LY344864 is used in combination with buspirone, or
LY344864 is used in combination with gepirone, or
LY344864 is used in combination with ipsapirone, or
LY344864 is used in combination with perospirone, or
LY344864 is used in combination with tandospirone, or
LY344864 is used in combination with befiradol, or
LY344864 is used in combination with repinotan, or
LY344864 is used in combination with piclozotan, or
LY344864 is used in combination with osemozotan, or
LY344864 is used in combination with flesinoxan, or
LY344864 is used in combination with flibanserin, or
LY344864 is used in combination with sarizotan or a pharmaceutically acceptable derivative thereof.

In a preferred embodiment of the present invention, COL-144 is used in combination with buspirone or gepirone.

In yet a preferred embodiment of the present invention, COL-144 is used in combination with tandospirone.

Movement Disorders

The present invention relates to treatment of movement disorders, such as disorders which are associated with altered or impaired synaptic dopamine levels. Movement disorders according to the present invention may be selected from the group of disorders comprising ataxia, akathisia, dystonia, essential tremor, Huntington's disease, myoclonus, Parkinson's disease, Rett syndrome, tardive dyskinesia, Tourette syndrome, Wilson's disease, dyskinesia, chorea, Machado-Joseph disease, restless leg syndrome, spasmodic torticollis, geniospasm, or movement disorders associated therewith.

Movement disorders according to the present invention may also be associated with use of neuroleptic drugs, idiopathic disease, genetic dysfuntions, infections or other conditions which lead to dysfunction of the basal ganglia and/or lead to altered synaptic DA levels.

In one preferred embodiment of the present invention, the treatment is of one or more movement disorders selected from group of akathisia, tarditive dyskinesia, Parkinson's disease, movement disorders associated with Parkinson's disease, such as bradykinesia, akinesia and dyskinesia for example L-DOPA induced dyskinesia.

Parkinson's disease is associated with muscle rigidity, tremor, postural abnormalities, gait abnormalities, a slowing of physical movement (bradykinesia), and in extreme cases a loss of physical movement (akinesia). PD is caused by degeneration and death of dopaminergic neurons in substantia nigra pars *compacta*, and leads to dysfunctional regulation of dopamine neurotransmission.

In one particularly preferred embodiment of the present invention the movement disorder is Parkinson's disease or associated movement disorders akinesia, dyskinesia and bradykinesia. Another particularly preferred embodiment of the present invention is treatment of movement disorders associated with Parkinson's disease such as L-DOPA induced dyskinesia. A third particularly preferred embodiment of the present invention is the treatment of movement disorders associated with Parkinson's disease such as akinesia.

In one preferred embodiment of the present invention, the movement disorder is tardive dyskinesia.

In another embodiment of the present invention, the movement disorder is caused by or associated with medication of antipsychotics such as haloperidol, droperidol, pimozide, trifluoperazine, amisulpride, risperidone, aripiprazole, asenapine, and zuclopenthixol, antidepressants such as fluoxetine, paroxetine, venlafaxine, and trazodone, antiemetic drugs such as dopamine blockers for example metoclopramide (reglan) and prochlorperazine (compazine).

In yet another embodiment of the present invention, the movement disorder is caused by or associated with withdrawal of opioids, barbiturates, cocaine, benzodiazepines, alcohol, or amphetamines.

Dosage

The combination of compounds and pharmaceutical compositions of the present invention induces combined or synergistic effects, which enable for a lowered dosage of 5-HT1 agonists in the treatment of movement disorders. The lowered dosage scheme further results in a reduced risk of adverse effects of treatment with 5-HT1 agonists, such as reducing the risk of developing serotonin syndrome.

According to the present invention, 5-HT1 agonists are administered to individuals in need of treatment in pharmaceutically effective doses. A therapeutically effective amount of a compound according to the present invention is an amount sufficient to cure, prevent, reduce the risk of, alleviate or partially arrest the clinical manifestations of a given disease or movement disorder and its complications. The amount that is effective for a particular therapeutic purpose will depend on the severity and the sort of the movement disorder as well as on the weight and general state of the subject. The 5-HT1 agonists of the present invention may be administered one or several times per day, such as from 1 to 4 times per day, such as from 1 to 3 times per day, such as from 1 to 2 times per day, wherein administration from 1 to 3 times per day is preferred.

In one embodiment of the present invention, the compound is either a) a combined 5-HT1B, 5-HT1D agonist and/or 5-HT1F agonist, or b) a selective 5-HT1D receptor agonist, or c) a selective 5-HT1F receptor agonist, and is administered in doses of 0.5 mg/day to 100 mg/day, such as 0.5 mg/day to 1 mg/day, such as 1 mg/day to 2 mg/day, such as 2 mg/day to 5 mg/day, or such as 5 mg/day to 10 mg/day, or such as 5 mg/day to 10 mg/day, or such as 10 mg/day to 20 mg/day, or such as 20 mg/day to 30 mg/day, or such as 30 mg/day to 40 mg/day, or such as 40 mg/day to 50 mg/day, or such as 40 mg/day to 60 mg/day, or such as 60 mg/day to 70 mg/day, or such as 70 mg/day to 80 mg/day, or such as 80 mg/day to 90 mg/day, or such as 90 mg/day to 95 mg/day, or such as 95 mg/day to 98 mg/day, or such as 98 mg/day to 100 mg/day.

In another embodiment of the present invention, the compound is either a) a combined 5-HT1B, 5-HT1D agonist and/or 5-HT1F agonist, or b) a selective 5-HT1D receptor agonist, or c) a selective 5-HT1F receptor agonist and is administered in doses of 0.5 mg/day to 200 mg/day, such as in the range of 0.5 mg/day to 60 mg/day, such as 0.05 mg/day to 0.1 mg/day, or such as 0.1 to 0.5 mg/day, or such as in the range of 0.5 mg/day to 60 mg/day, such as in the range of 0.5 to 30 mg/day, such as such as 0.5 to 5 mg/day, or such as 5 mg/day to 10 mg/day, or such as 10 mg/day to 15 mg/day, or such as 15 mg/day to 30 mg/day.

In a preferred embodiment of the present invention, the compound is either a) a combined 5-HT1B, 5-HT1D receptor agonist and/or 5-HT1F receptor agonist, or b) a selective 5-HT1D receptor agonist, or c) a selective 5-HT1F receptor agonist and is administered in doses of 0.5 mg/day to 200 mg/day, preferably in doses of 0.5 mg/day to 60 mg/day and even more preferably in doses of 0.5 mg/day to 10 mg/day.

In yet a preferred embodiment of the present invention, zolmitriptan is administered in doses of 0.5 mg/day to 30 mg/day and more preferably in doses of 0.5 mg/day to 10 mg/day.

In one embodiment of the present invention, a single dose of the compound that is either a) a combined 5-HT1B, 5-HT1D receptor agonist and/or 5-HT1F receptor agonist, or b) a selective 5-HT1D receptor agonist, or c) a selective 5-HT1F receptor agonist are administered and may comprise of 0.05 mg/kg bodyweight to 100 mg/kg bodyweight, such as in the range of 0.05 mg/kg bodyweight to 20 mg/kg bodyweight, such as 0.05 mg/kg bodyweight to 0.1 mg/kg bodyweight, or such as 0.1 to 0.5 mg/kg bodyweight, or such as in the range of 0.5 mg/kg bodyweight to 10 mg/kg bodyweight, such as such as 0.5 mg/kg bodyweight to 1 mg/kg bodyweight, such as 1 mg/kg bodyweight to 2 mg/kg bodyweight, such as 2 mg/kg bodyweight to 5 mg/kg bodyweight, or such as 5 mg/kg bodyweight to 10 mg/kg bodyweight.

In a preferred embodiment a single dose of the compound that is either a) a combined 5-HT1B, 5-HT1D receptor agonist and/or 5-HT1F receptor agonist, or b) a selective 5-HT1D receptor agonist, or c) a selective 5-HT1F receptor agonist is in the range of 0.05 mg/kg bodyweight to 10 mg/kg bodyweight.

According to the present invention, a compound which is a combined 5-HT1B, 5-HT1D agonist and/or 5-HT1F agonist can have different affinity and/or receptor activation efficacy for the different 5-HT1 receptors. Thus, when using certain doses of such compounds, it may be possible to stimulate the 5-HT1 receptors do different extends, due to a more efficient activation of one type of 5-HT1 receptor than another type of 5-HT1 receptor. For instance some doses of compounds may trigger responses from only one 5-HT1 receptor, or some doses of compounds may trigger a moderate response from one 5-HT receptor, while another type of 5-HT1 receptor is triggered to result in a full response, or a minimal response. One method for measuring the extent of receptor activation is to measure the response at a certain dose relative to the full response (Emax).

In one embodiment of the present invention, a compound is used in doses wherein said dose mediates an activation of the 5-HT1D receptor which is higher than the activation of the 5-HT1B receptor. Thus, the measured response of the 5-HT1B receptor compared to the 5-HT1D receptor can be in the range of 1% to 99% of the response of the 5-HT1D receptor, such as in the range of 1% to 15%, such as 1% to 10%, or such as 10% to 15%, or such as in the range of 15% to 35%, such as 15% to 25%, or such as 25% to 35%, such as in the range of 35% to 55%, such as 35% to 45%, or such as 45% to 55%, or such as in the range of 55% to 75%, such as 55% to 65%, or such as 65% to 75%, or such as in the range of 95% to 99%, such as 95% to 97%, or such as 97% to 98%, or such as 98% to 99%.

The present invention relates to dosages of 5-HT1A agonists which are administered in doses of 0.5 mg/day to 100 mg/day, such as 0.5 mg/day to 1 mg/day, such as 1 mg/day to 2 mg/day, such as 2 mg/day to 5 mg/day, or such as 5 mg/day to 10 mg/day, or such as 5 mg/day to 10 mg/day, or such as 10 mg/day to 20 mg/day, or such as 20 mg/day to 30 mg/day, or such as 30 mg/day to 40 mg/day, or such as 40 mg/day to 50 mg/day, or such as 40 mg/day to 60 mg/day, or such as 60 mg/day to 70 mg/day, or such as 70 mg/day to 80 mg/day, or such as 80 mg/day to 90 mg/day, or such as 90 mg/day to 95 mg/day, or such as 95 mg/day to 98 mg/day, or such as 98 mg/day to 100 mg/day.

The 5-HT1A receptor agonist can according to the present invention be administered in doses in the range of 0.05 mg/day to 500 mg/day, such as 0.05 mg/day to 0.1 mg/day, such as 0.1 mg/day to 0.5 mg/day, preferably in the range of 0.5 mg/day to 100 mg/day, and even more preferably in the range of 0.5 mg/day to 30 mg/day, such as 0.5 mg/day to 1 mg/day, or such as 1 mg/day to 2 mg/day, or such as 2 mg/day to 5 mg/day, or such as 5 mg/day to 10 mg/day, or such as 10 mg/day to 15 mg/day, or such as 15 mg/day to 20 mg/day, or such as 20 mg/day to 30 mg/day.

In a preferred embodiment of the present invention, a single dose of 5-HT1A agonist is in the range of 0.5 to 100 mg/day and even more preferred in doses of 0.5 to 30 mg/day.

In a preferred embodiment of the present invention, the 5-HT1A agonist is administered in doses of 0.5 mg/day to 100 mg/day and the compound is a combined agonist of two or more of the 5-HT1B, the 5-HT1D and the 5-HT1F receptors, or a selective 5-HT1D agonist, or a selective 5-HT1F agonist and is administered in doses of 0.1 mg/day to 60 mg/day, even more preferably the 5-HT1A agonist is administered in doses of 0.5 mg/day to 30 mg/day and the compound is a combined agonist of two or more of the 5-HT1B, the 5-HT1D and the 5-HT1F receptors, or a selective 5-HT1D agonist, or a selective 5-HT1F agonist and is administered in doses of 0.1 mg/day to 10 mg/day.

In yet a preferred embodiment of the present invention, buspirone is administered in doses of 0.5 mg/day to 100 mg/day and zolmitriptan is administered in doses of 0.5 mg/day to 60 mg/day, and even more preferably, buspirone is administered in doses of 0.5 to 30 mg/day and zolmitriptan is administered in doses of 0.5 to 10 mg/day.

In one embodiment of the present invention, a single dose of 5-HT1A receptor agonist can be in the range of 0.05 mg/kg bodyweight to 100 mg/kg bodyweight, such as in the range of 0.05 mg/kg bodyweight to 20 mg/kg bodyweight, such as 0.05 mg/kg bodyweight to 0.1 mg/kg bodyweight, or such as 0.1 to 0.5 mg/kg bodyweight, or such as in the range of 0.5 mg/kg bodyweight to 10 mg/kg bodyweight, such as such as 0.5 mg/kg bodyweight to 1 mg/kg bodyweight, such as 1 mg/kg bodyweight to 2 mg/kg bodyweight, such as 2 mg/kg bodyweight to 5 mg/kg bodyweight, or such as 5 mg/kg bodyweight to 10 mg/kg bodyweight.

In a preferred embodiment a single dose of the 5-HT1A agonist is in the range of 0.05 mg/kg bodyweight to 10 mg/kg bodyweight.

Second Active Ingredients

The compounds or pharmaceutical compositions of the present invention may be combined with or comprise one or more second active ingredients which are understood as other therapeutical compounds or pharmaceutically acceptable derivatives thereof. In one particularly preferred embodiment of the present invention, a 5-HT1A agonist as mentioned herein is regarded as a second active ingredient.

A second active ingredient according to the present invention may further be one or more agents selected from the group of agents increasing the dopamine concentration in the synaptic cleft, dopamine, L-DOPA or dopamine receptor agonists or derivatives thereof. Thus, according to the present invention second active ingredients comprise DA receptor agonists, such as bromocriptine, pergolide, pramipexole, ropinirole, piribedil, cabergoline, apomorphine, lisuride, and derivatives thereof.

Second active ingredients may further be selected from the group of compounds which ameliorate PD symptoms or which are used for treatment of PD, such as peripheral inhibitors of the transformation of L-DOPA or (other dopamine prodrugs) to dopamine, for example decarboxylase inhibitors such as carbidopa or benserazide, or NMDA antagonists such as for example amatidine (Symmetrel), catechol-O-methyl transferase (COMT) inhibitors such as for example tolcapone and entacapone, MAO-B inhibitors such as for example selegiline and rasagiline, serotonin receptor modulators, kappa opioid receptors agonists such as for example TRK-820 ((E)-N-[17-cyclopropylmethyl)-4,5α-epoxy-3,14-dihydroxymorphinan-6β-yl]-3-(furan-3-yl)-N-methylprop-2-enamide monohydrochloride), GABA modulators, modulators of neuronal potassium channels such as flupirtine and retigabine, and glutamate receptor modulators.

In a preferred embodiment of the present invention, a second active ingredient is a dopamine prodrug, such as L-DOPA or a pharmaceutically acceptable derivative thereof. Thus in one preferred embodiment, L-DOPA is used in combination with a combined 5-HT1B and 5-HT1D receptor agonist selected from the group of zolmitriptan and frovatriptan or a pharmaceutically acceptable derivative thereof, and a 5-HT1A receptor agonist selected from buspirone, tandospirone or gepirone or a pharmaceutically acceptable derivative thereof, Even more preferably L-DOPA is used in combination with zolmitriptan and buspirone or a pharmaceutically acceptable derivative thereof.

In one embodiment of the present invention, the compounds or pharmaceutical compositions may be combined with two or more second active ingredients. Such two second active ingredients may be L-DOPA in combination with a decarboxylase inhibitor. Thus in an embodiment of the present invention, the two or more second active ingredients comprise L-DOPA and carbidopa, or L-DOPA and benserazide.

In another embodiment, such two second active ingredients are L-DOPA in combination with a COMT inhibitor, wherein the COMT inhibitor can be tolcapone, or entacapone.

The second active ingredients according to the present invention can also be included in the same formulations such as for example the L-DOPA/benserazide formulations sinemet, parcopa, madopar, or L-DOPA/COMT inhibitor formulations such as for example stalevo.

Methods of Treatment

The present invention provides methods for treatment, prevention or alleviation of movement disorders as mention herein. Such methods according to the present invention comprise one or more steps of administration of an effective amount of a pharmaceutical composition or a compound according to the present invention to an individual in need thereof. Such steps of administration may be simultaneous, sequential or separate.

In a preferred method of treatment according to the present invention, the compound or pharmaceutical composition comprises zolmitriptan, frovatriptan, eletriptan or COL144 or pharmaceutically acceptable derivative thereof, more preferably the compound or pharmaceutical composition comprises zolmitriptan or pharmaceutically acceptable derivative thereof.

Methods for treatment according to the present invention may further comprise one or more steps of administration of one or more second active ingredients as defined herein.

In one particular embodiment of the present invention, the pharmaceutical composition or the compound as defined herein is administered simultaneously, sequentially or separately in combination with an effective amount of a 5-HT1A agonist.

In a preferred embodiment of the present invention, the pharmaceutical composition or compound as defined herein is administered simultaneously, sequentially or separately in combination with an effective amount of a 5-HT1A agonist selected from the group of alnespirone, binospirone, buspirone, gepirone, ipsapirone, perospirone, tandospirone, befiradol, repinotan, piclozotan, osemozotan, flesinoxan, flibanserin and sarizotan or a derivative thereof.

In a more preferred embodiment of the present invention, buspirone, tandospirone or gepirone or a derivative thereof is used in a method of treatment.

In a most preferred embodiment of the present invention, the 5-HT1A agonist is buspirone or pharmaceutically acceptable derivative thereof.

Thus, in a most preferred method of the present invention, the compound or pharmaceutical composition comprises zolmitriptan or a pharmaceutically acceptable derivative thereof and the 5-HT1A agonist is buspirone or pharmaceutically acceptable derivative thereof.

In methods of the present invention, a compound or a pharmaceutical composition according to the present invention may be administered alone or in combination with one or more other second active ingredients, either concomitantly or sequentially, and in any suitable ratios. Such second active ingredients may, for example, be selected from compounds used to treat or prevent Parkinson's disease or symptoms and complications associated with Parkinson's disease.

Methods of treatment according to the present invention may include a step wherein the pharmaceutical composition or compound as defined herein is administered simultaneously, sequentially or separately in combination with one or more second active ingredients as defined herein.

In a preferred embodiment of the present invention, a second active ingredient used in a method provided by the invention is a dopamine prodrug, such as L-DOPA.

Thus in one preferred embodiment, the second active ingredient L-DOPA is used in combination with a combined 5-HT1B and 5-HT1D receptor agonist selected from the group of zolmitriptan and frovatriptan or a pharmaceutically acceptable derivative thereof, and a 5-HT1A receptor agonist selected from buspirone, tandospirone or gepirone or a pharmaceutically acceptable derivative thereof, Even more preferably L-DOPA is used in combination with zolmitriptan and buspirone or a pharmaceutically acceptable derivative thereof.

In the methods for treatment according to the present invention, the compounds or pharmaceutical compositions as defined herein are administered in doses as referred to herein.

Further, in the methods for treatment according to the present invention, the 5-HT1A agonist is administered in doses as referred to herein.

The administration of compounds, pharmaceutical compositions and second active ingredients according to the present invention may be administered to an individual during at various time points of treatment. The treatment may be done over one continued period, or in intervals with periods in between wherein the administration of one or more compounds, pharmaceutical compositions and second active ingredients according to the present invention is stopped, decreased or altered. Such treatment periods or non-treatment periods may vary in length, and can be from 1 day to 60 days, such as 1 to 3 days, 3 to 6 days, 6 to 8 days, 8 to 14 days, 14 to 21 days, 21 to 30 days, 30 to 42 days, 42 to 49 days or 49 to 60 days.

Kit of Parts

The present invention provides kits of parts which can be useful for treatment of movement disorders as described herein.

A kit of parts according to the present invention comprises one or more of the pharmaceutical compositions or compounds as defined herein for treatment, prevention or alleviation of movement disorders. Kits according to the present invention allows for simultaneous, sequential or separate administration of the pharmaceutical compositions, compounds or second active ingredients described herein.

In one embodiment of the present invention, the kit of parts comprises one or more second active ingredients as described herein.

In a preferred embodiment of the present invention, the kit of parts comprises a 5-HT1A agonist such as for example alnespirone, binospirone, buspirone, gepirone, ipsapirone, perospirone, tandospirone, befiradol, repinotan piclozotan, osemozotan, flesinoxan, flibanserin and sarizotan or a derivative thereof.

In a highly preferred embodiment of the present invention, the kits of parts comprises buspirone, tandospirone or gepirone or a derivative thereof.

In a most preferred method of the present invention, the compound or pharmaceutical composition comprises zolmitriptan or a pharmaceutically acceptable derivative thereof, and the 5-HT1A agonist is buspirone or pharmaceutically acceptable derivative thereof.

In a preferred embodiment of the present invention, a second active ingredient comprised in a kit provided by the invention is a dopamine prodrug, such as L-DOPA.

Thus in one preferred embodiment, a kit of parts comprises a combined 5-HT1B and 5-HT1D receptor agonist selected from the group of zolmitriptan and frovatriptan or a pharmaceutically acceptable derivative thereof, and can further comprise a 5-HT1A receptor agonist selected from buspirone, tandospirone or gepirone or a pharmaceutically acceptable derivative thereof, and a second active ingredient selected from L-DOPA or a pharmaceutically acceptable derivative thereof.

Method of Preparation

The present invention provides methods for the preparation of the pharmaceutical compositions as defined herein.

A method for preparation according to the present invention may comprise at least a step wherein a) either a combined 5-HT1B, 5-HT1D agonist and/or 5-HT1F receptor agonist, or a selective 5-HT1D receptor agonist or a selective 5-HT1F receptor agonist, is mixed with b) a 5-HT1A agonist to produce a composition which comprises one or more of c) selective 5-HT1A agonist, and d) a combined 5-HT1B, 5-HT1D agonist and/or 5-HT1F agonist, or a selective 5-HT1F receptor agonist or a selective 5-HT1F receptor agonist.

The methods for preparation may further comprise a step wherein compounds for formulation as mentioned herein are added to a mixture of one or more of a) selective 5-HT1A agonists, and one or more of b) compounds which are combined 5-HT1B, 5-HT1D agonist and/or 5-HT1F agonist, or a selective 5-HT1D receptor agonist, or a selective 5-HT1F agonist.

A method for preparation according to the present invention may comprise at least a step wherein a) either a combined 5-HT1B, 5-HT1D agonist and/or 5-HT1F receptor agonist, or a selective 5-HT1D receptor agonist or a selective 5-HT1F receptor agonist, is mixed with b) a 5-HT1A agonist to produce a composition which comprises one or more of c) a partial or selective 5-HT1A agonist, and d) a combined 5-HT1B, 5-HT1D agonist and/or 5-HT1F agonist, or a selective 5-HT1F receptor agonist or a selective 5-HT1F receptor agonist.

The methods for preparation may further comprise a step wherein compounds for formulation as mentioned herein are added to a mixture of one or more of a) a partial or selective 5-HT1A agonists, and one or more of b) compounds which are combined 5-HT1B, 5-HT1D agonist and/or 5-HT1F agonist, or a selective 5-HT1D receptor agonist, or a selective 5-HT1F agonist.

In one preferred embodiment of the present invention a method for preparation according to the present invention may comprise at least a step wherein a) one or more combined 5-HT1B, 5-HT1D agonist and/or 5-HT1F receptor agonist selected from the group of zolmitriptan, rizatriptan, naratriptan and frovatriptan is mixed with b) one or more 5-HT1A agonists selected from the group if buspirone, tandospirone or gepirone to produce a composition comprising one or more which comprises one or more of combined 5-HT1B, 5-HT1D agonist and/or 5-HT1F receptor agonist and one or more 5-HT1A agonists.

In a more preferred embodiment of the present invention, a method for preparation according to the present invention may comprise at least a step wherein a) zolmitriptan is mixed with a composition comprising b) buspirone, to produce a composition comprising both zolmitriptan and buspirone.

Routes of Administration

It will be appreciated that the preferred route of administration will depend on the general condition and age of the subject to be treated, the nature of the condition to be treated, the location of the tissue to be treated in the body and the active ingredient chosen.

In one embodiment of the present invention, the route of administration allows for the agent to cross the blood-brain barrier.

Systemic Treatment

Systemic treatment according to the present invention the route of administration is capable of introducing the agent into the blood stream to ultimately target the sites of desired action.

Such routes of administration are any suitable routes, such as an enteral route, the oral, rectal, nasal, pulmonary, buccal, sublingual, transdermal, intracisternal, intraperitoneal, and parenteral (including subcutaneous, intramuscular, intrathecal, intravenous and intradermal) route, wherein the oral route is preferred.

Appropriate dosage forms for such administration may be prepared by conventional techniques.

Oral Administration

Oral administration is normally for enteral drug delivery, wherein the agent is delivered through the enteral mucosa.

In a preferred embodiment of the present invention, the compounds and pharmaceutical compositions as defined herein are administered orally.

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration, subcutaneous administration. Furthermore, parenteral administration includes inhalations and topical administration.

Accordingly, the agent may be administered topically to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent may be administered topically to cross the skin.

The subcutaneous and intramuscular forms of parenteral administration are generally preferred.

Local Treatment

The agent according to the invention may be used as a local treatment, ie. be introduced directly to the site(s) of action as will be described below.

Accordingly, the agent may be applied to the skin or mucosa directly, or the agent may be injected into the site of action, for example into the diseased tissue or to an end artery leading directly to the diseased tissue.

Pharmaceutical Formulations

The 5-HT1 agonists or pharmaceutically acceptable derivatives thereof of the present invention may be administered alone or in combination with pharmaceutically acceptable carriers or excipients, in either single or multiple doses. The pharmaceutical compositions or compounds according to the invention may be formulated with pharmaceutically acceptable carriers or diluents as well as any other known adjuvants and excipients in accordance with conventional techniques such as those disclosed in Remington: The Science and Practice of Pharmacy, 20$^{th}$ Edition, Gennaro, Ed., Mack Publishing Co., Easton, Pa., 2000.

The pharmaceutical composition may be specifically formulated for administration by any suitable route, such as an enteral route, the oral, rectal, nasal, pulmonary, buccal, sublingual, transdermal, intracisternal, intraperitoneal, and parenteral (including subcutaneous, intramuscular, intrathecal, intravenous and intradermal) route, wherein the oral route is preferred.

In a preferred embodiment of the present invention, the pharmaceutical compositions or compounds of the present invention are formulated for crossing the blood-brain-barrier.

Pharmaceutical compositions for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use. Depot injectable formulations are also regarded as being within the scope of the present invention.

Other suitable administration forms include suppositories, sprays, ointments, cremes, gels, inhalants, dermal patches, implants, etc.

A compound or a 5-HT1 agonist for use according to the present invention is generally utilized as the free substance or as a pharmaceutically derivative such as a pharmaceutically acceptable ester or such as a salt thereof. Examples of the latter are: an acid addition salt of a compound having a free base functionality, and a base addition salt of a compound having a free acid functionality. The term "pharmaceutically acceptable salt" refers to a non-toxic salt of a compound for use according to the present invention, which salts are generally prepared by reacting a free base with a suitable organic or inorganic acid, or by reacting an acid with a suitable organic or inorganic base. When a compound for use according to the present invention contains a free base functionality, such salts are prepared in a conventional manner by treating a solution or suspension of the compound with a chemical equivalent of a pharmaceutically acceptable acid. When a compound for use according to the present invention contains a free acid functionality, such salts are prepared in a conventional manner by treating a solution or suspension of the compound with a chemical equivalent of a pharmaceutically acceptable base. Physiologically acceptable salts of a compound with a hydroxy group include the anionic form of the compound in combination with a suitable cation, such as sodium or ammonium ion. Other salts which are not pharmaceutically acceptable may be useful in the preparation of compounds of the invention, and these form a further aspect of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

In a specific embodiment, compounds of the present invention are used as acid addition salts formed with mineral acids such as hydrochloric acid and hydrobromic acid, and, especially, hydrochloric acid. An example of such a salt is for example buspirone hydrochloride.

In one embodiment of the present invention, the 5-HT1 agonists of the present invention is on crystalline forms, for example co-crystallized forms or hydrates of crystalline forms.

The term "prodrug" refers to compounds that are rapidly transformed in vivo to yield the parent compound of the above formulae, for example, by hydrolysis in blood or by metabolism in cells, such as for example the cells of the basal ganglia. A thorough discussion is provided in T. Higuchi and V Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference. Examples of prodrugs include pharmaceutically acceptable, non-toxic esters of the compounds of the present invention. Esters of the compounds of the present invention may be prepared according to conventional methods "March's Advanced Organic Chemistry, 5$^{1'}$ Edition". M. B. Smith & J. March, John Wiley & Sons, 2001.

For parenteral administration, solutions of compounds for use according to the present invention in sterile aqueous solution, in aqueous propylene glycol or in sesame or peanut oil may be employed. Aqueous solutions should be suitably buffered where appropriate, and the liquid diluent rendered isotonic with, e.g., sufficient saline or glucose. Aqueous solutions are particularly suitable for intravenous, intramuscular, subcutaneous and intraperitoneal administration. The sterile aqueous media to be employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Moreover, the carrier or diluent may include any sustained release material known in the art, such as glyceryl monostearate or glyceryl distearate, alone or mixed with a wax. The pharmaceutical compositions formed by combining the compounds for use according to the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units, such as capsules or tablets, which each contain a predetermined amount of the active ingredient, and which may include a suitable excipient.

Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents and preserving agents in order to provide pharmaceutically elegant and palatable preparations. Tablets may contain the active ingredient(s) in admixture with non-toxic pharmaceutically acceptable excipients which are suitable for the manufacture of tablets. These excipients may, for example, be: inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, the contents of which are incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsules wherein the active ingredient is mixed with water or an oil medium, for example peanut oil, liquid paraffin, or olive oil.

Aqueous suspensions may contain the compound for use according to the present invention in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising compounds for use according to the present invention may also be in the form of oil-in-water emulsions. The oily phase may be a vegetable oil, for example, olive oil or *arachis* oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include, for example, cocoa butter and polyethylene glycols.

For buccal and sublingual use, creams, ointments, jellies, solutions of suspensions, etc., containing the compounds of the invention may be employed. In the context of the present invention, formulations for buccal and sublingual application include mouth washes and gargles.

Compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some compounds of the present invention may form solvates with water or common organic solvents. Such solvates are also encompassed within the scope of the invention.

Thus, a further embodiment provides a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form, or may be in the form of a troche or lozenge. The amount of solid carrier will vary widely, but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ®IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition comprising a compound according to the present invention may comprise a compound according to the present invention in combination with further active substances, such as those described in the foregoing.

The present invention also provides methods for the preparation of compounds for use according to the present invention.

EXAMPLES

The potency and efficacy of the present invention can be determined using different pharmacological procedures. The present invention is further illustrated with reference to the following examples, which are not intended to be limiting in any way to the scope of the invention as claimed.

Example I

Determination of Activation of the Serotonin

5-HT1A, 5-HT1B, 5-HT1D and 5-HT1F Receptors

The [$^{35}$S]-GTPγS assay is used to determine the effects of the compounds of the present invention on the serotonin 5-HT1A, 5-HT1B, 5-HT1D and 5-HT1F receptors.

Membrane Preparation

Assays are performed with cells expressing the cloned human 5-HT1A, 5-HT1B, 5-HT1D, 5-HT1E or 5-HT1F receptor. On the assay day, an aliquot of cells (stored at −70° C.) is thawed and re-suspended in 50 mM Tris-HCl, pH 7.4, and centrifuged at 39,800 g for 10 min at 4° C. The resulting pellet is re-suspended in 50 mM Tris-HCl, pH 7.4, incubated for 10 min at 37° C., and centrifuged at 39,800 g for 10 min at 4° C.

The pellet is re-suspended and centrifuged once more, with the final pellet being suspended in 4 mM $MgCl_2$, 160 mM NaCl, 0.267 mM EGTA, 67 mM Tris-HCl, pH 7.4 for the [$^{35}$S]-GTPgS binding assays.

Binding Assay

The methods for the 5-HT1A, 5-HT1B, 5-HT1D, 5-HT1E or 5-HT1F receptor [$^{35}$S]-GTPgS binding assays, are adapted to an SPA (scintillation proximity assay) format. Incubations are performed in a total volume of 200 ml in 96-well assay plates. [$^{35}$S]-GTPγS and guanosine-50-diphosphate (GDP) in assay buffer ($MgCl_2$, NaCl, EGTA in Tris-HCl, pH 7.4; 50 ml) is added to 50 ml of test compounds diluted in water. WGA (wheat germ agglutinin) beads (Amersham Pharmacia Biotech Inc., Piscataway, N.J., USA) for SPA in assay buffer (50 ml) are then added. Membrane homogenate (50 ml) from cells expressing the cloned human 5-HT1A, 5-HT1B, 5-HT1D, 5-HT1E or 5-HT1F receptor in assay buffer is added, and the plates are covered with sealing tape (Perkin Elmer Wallac, Inc., Gaithersburg, Md., USA) and allowed to incubate at room temperature for 2 h.

The final concentrations of $MgCl_2$, NaCl, EGTA, GDP, [$^{35}$S]-GTPγS, and Tris are 3 mM, 120 mM, 0.2 mM, 10 mM, approximately 0.3 nM, and 50 mM, respectively. The plates are then centrifuged at approximately 200 g for 10 min at room temperature. The amount of [$^{35}$S]-GTPγS bound to the membranes, i.e. in close proximity to the WGA SPA beads, is then determined using a Wallac MicroBeta® Trilux Scintillation Counter (Perkin Elmer Wallac, Inc.).

Data Analysis

Using GraphPad Prism software, non-linear regression analysis is performed on the concentration-response curves (generating $EC_{50}$ and Emax values for stimulation of [$^{35}$S]-GTPγS binding) using a four-parameter logistic equation. Efficacy (Emax) values, determined by the non-linear regression analysis, for the selected compounds, is expressed as the percentage of [$^{35}$S]-GTPγS binding relative to the response produced by 10 mM of agonists for the (5-HT1A, 5-HT1B, 5-HT1E or 5-HT1F receptors or 1 mM 5-HT agonist for the 5-HT1D receptor which is run as a standard with each concentration-response curve.

Example II

Evaluation of 5-HT1 Agonists for Treatment of Movement Disorders Associated with Parkinson's Disease and LID The 6-OHDA Rat Model 6-OHDA (6-hydroxydopamine) is a neurotoxin that selectively kills dopaminergic and noradrenergic neurons and induces a reduction of dopamine levels in the brain. Administration of L-DOPA to unilaterally 6-OHDA-lesioned rats induces abnormal involuntary movements (AIMs). These are axial, limb and oral movements that occur only on the body side that is ipsilateral to the lesion. AIM rat models have been shown useful because they respond to a number of drugs which have been shown to suppress dyskinesia (including PD) in humans.

The 6-OHDA rat model is also useful for studying other movement disorders associated with Parkinson's disease, such as akinesia and decreased motor performance and coordination.

Test Procedure:

Animals: 90 experimentally-naïve, male, Sprague-Dawley rats at body weight of 200 to 250 g from Shanghai SLAC Co. Ltd. arrive at the laboratory at least 1 week prior to behavioural testing. Rats are housed in groups of n=2/cage. Animals have ad libitum access to standard rodent chow and water. Animal housing and testing rooms are maintained under controlled environmental conditions and are within close proximity of each other. Animal housing rooms are on a 12-hour light-dark cycle with lights on at 6:00 AM and maintained at 70° F./21° C. (range: 68-72° F./20-22° C.) with a humidity range of 20-40%. Testing rooms are maintained at 68-72° F. with a humidity range of 20-40%.

6-OHDA Lesion Surgery:

DA-denervating lesions are performed by unilateral injection of 6-OHDA in the ascending nigrostriatal pathway. Rats were anesthetized with pentobarbital sodium 40 mg/kg (i.p.) and positioned in a stereotactic frame. 6-OHDA is injected into the right ascending DA bundle at the following coordinates (in mm) relative to bregma and dural surface: (1) toothbar position −2.3, A=−4.4, L=1.2, V=7.8, (7.5 ug 6-OHDA), (2) toothbar position+3.4, A=−4.0, L=0.8, V=8.0 mm (6 ug 6-OHDA). The neurotoxin injections are performed at a rate of 1 ul/min, and the injection cannula is left in place for an additional 2-3 min thereafter. Two weeks after surgery rats with nearly complete (>90%) lesions are selected by means of an amphetamine-induced rotation test. The animals are placed in plastic Perspex bowls (30 cm in diameter) and the rotational behavior (360° turns) is recorded by an automated rotometer for 90 min after the i.p. injection of 2.5 mg/kg d-amphetamine sulphate. Animals exhibiting 56 full body turns/min towards the side of DA deficiency are included in the study. Animals are then allocated into two well-matched sub-groups (according to the amphetamine rotation) and receive daily treatment as described below.

Drugs and Treatment Regimens

Drug Treatment:

L-DOPA methyl ester (Sigma-Aldrich, Germany) is given at the dose of 6 mg/kg/day, combined with 15 mg/kg/day of benserazide HCl (Sigma-Aldrich, Germany). Chronic treatment with this dose of L-DOPA and benserazide is given for 3 weeks to all the rats with good lesions in order to induce a gradual development of dyskinetic-like movements. Thereafter, rats that have not developed dyskinesia are excluded from the study, and the rats with a cumulative AIM score ≥28 points over five testing sessions (dyskinesia severity ≥grade 2 on each axial, limb and orolingual scores) are kept on a drug treatment regimen of at least two injections of L-DOPA/benserazide per week in order to maintain stable AIM scores. The selected rats are allocated groups of 9-12 animals each, which are balanced with the respect to AIM severity. The animals are then treated with the drug and drug combinations as described below.

Prevention:

In the prevention study rats are treated with L-DOPA methyl ester (6 mg/kg i.p. plus benserazide 15 mg/kg) in combination with buspirone (0.5-10 mg/kg/day) and zolmitriptan (0.5 mg/kg/day-20 mg/kg/day i.p.) given at the same time of L-DOPA, for 3 weeks. At the end of this treatment (treatment period 1), animals received a low dose of apomorphine (0.02 mg/kg, s.c.) and tested for apomorphine-induced AIMs in order to investigate the sensitization state of the DA receptors. Treatments are then continued so that animals are treated only with L-DOPA for an additional two weeks (treatment period 2). Animals are injected daily and tested every second day for L-DOPA-induced dyskinesia throughout the experimental periods 1 and 2 and then sacrificed for HPLC analysis of DA, serotonin and metabolites.

L-DOPA Induced AIMs and Drugs Screening Test

AIMs ratings are performed by an investigator who was kept unaware of the pharmacological treatment administered to each rat (experimentally blinded). In order to quantify the severity of the AIMs, rats are observed individually in their standard cages every 20th minute at 20-180 min after an injection of l-DOPA. The AIM's are classified into four subtypes:

(A) axial AIMs, i.e., dystonic or choreiform torsion of the trunk and neck towards the side contralateral to the lesion. In the mild cases: lateral flexion of the neck or torsional movements of the upper trunk towards the side contralateral to the lesion. With repeated injection of L-DOPA, this movement may develop into a pronounced and continuous dystonia-like axial torsion.

(B) limb AIMs, i.e., jerky and/or dystonic movements of the forelimb contralateral to the lesion. In mild cases: hyperkinetic, jerky stepping movements of the forelimb contralateral to the lesion, or small circular movements of the forelimb to and from the snout. As the severity of dyskinesia increases (which usually occurs with repeated administration of L-DOPA), the abnormal movements increase in amplitude, and assume mixed dystonic and hyperkinetic features. Dystonic movements are caused by sustained co-contraction of agonist/antagonist muscles; they are slow and force a body segment into unnatural positions. Hyperkinetic movements are fast and irregular in speed and direction. Sometimes the forelimb does not show jerky movements but becomes engaged in a continuous dystonic posture, which is also scored according to the time during which it is expressed.

(C) orolingual AIMs, i.e., twitching of orofacial muscles, and bursts of empty masticatory movements with protrusion of the tongue towards the side contralateral to the lesion. This form of dyskinesia affects facial, tongue, and masticatory muscles. It is recognizable as bursts of empty masticatory movements, accompanied to a variable degree by jaw opening, lateral translocations of the jaw, twitching of facial muscles, and protrusion of the tongue towards the side contralateral to the lesion. At its extreme severity, this subtype of dyskinesia engages all the above muscle groups with notable strength, and may also become complicated by self-mutilative biting on the skin of the forelimb contralateral to the lesion (easily recognizable by the fact that a round spot of skin becomes devoid of fur.

(D) locomotive AIMs, i.e., increased locomotion with contralateral side bias. The latter AIM subtype was recorded in conformity with the original description of the rat AIM scale, although it was later established that locomotive AIMs do not provide a specific measure of dyskinesia, but rather provide a correlate of contralateral turning behaviour in rodents with unilateral 6-OHDA lesions. Each of the four subtypes are scored on a severity scale from 0 to 4, where 0=absent, 1=present during less than half of the observation time, 2=present for more than half of the observation time, 3=present all the time but suppressible by external stimuli, and 4=present all the time and not suppressible by external stimuli. Axial, limb and orolingual AIMs are found to be modulated in a similar way by all the tested substances. Therefore, scores from these three AIM subtypes are summed. The sum of either locomotive axial, limb, and orolingual or axial, limb, and orolingual AIM scores per testing session are used for statistical analyses.

The results of the drug screening test show that buspirone (1 mg/kg/day i.p.) in combination with zolmitriptan (1 mg/kg/day i.p. or 5 mg/kg/day) significantly reduces L-DOPA-induced dyskinesia.

Below are a number of test which have the purpose of testing the compounds for side effects, such as reduced motor performance:

As mentioned above 6-OHDA-lesioned rats can also be used for as a model for other movement disorders associated with Parkinson's disease, such as bradykinesia, akinesia and decreased motor performance and coordination in these rats. Treatment with L-DOPA has beneficial effects on these movement disorders induced in the 6-OHDA-lesioned rats for example by preventing or reducing akinesia. It is of interest to test whether the combinations of compounds of the present invention have negative effects or impair the ability of L-DOPA to improve akinesia, decreased motor performance and coordination.

Rotarod Test

The rotarod test is performed after the administration of L-DOPA plus the doses of buspirone and zolmitriptan under investigation, or L-DOPA plus vehicle, using the same crossover design that was applied in the AIMs ratings sessions. The rotarod test serves the purpose of detecting potential deleterious effects of the compounds studied on the rats' motor performance and coordination. The rotarod test is performed using a previously described protocol (e.g. Dekundy et al: Behavioural Brain Research 179 (2007) 76-89). In brief, the animals are placed on the accelerating rod apparatus at an initial speed of 4 rotations per minute (rpm), with the speed increasing gradually and automatically to 40 rpm over 300 s. The animals are pre-trained to reach a stable performance in this test before initiating the drug screening studies. The training consisted of three sessions on 3 consecutive days, and each session included two separate testing trials. Between the testing sessions, the animals are given a shorter "motivational session" where the rod speed is increased from 4 to 14 rpm of 25 s only. Animals can stay on the rod for the entire 25 s in these low-speed sessions, which has been shown to have a positive effect on the animals' willingness to perform in this test. To maintain the alertness of the animals during all the testing sessions, the animals are tapped on their tails several times by the experimenter. In the drug-screening experiments, the animals are placed on the rod at 45-60 min interval after L-DOPA administration (i.e., at the time when central levels of L-DOPA reach their peak. The rotarod performance is expressed as total number of seconds spent on the accelerating rod. Buspirone (1 mg/kg/day i.p.) in combination with zolmitriptan (1 mg/kg/day i.p. or 5 mg/kg/day i.p.) only have limited effects on performance in the rotarod model, when compared to the rats treated only with L-DOPA (i.e. the performance was the similar), showing that motor performance and coordination is not significantly reduced in rats after administration of the compounds, and that in the rotarod test the combination of buspirone (1 mg/kg/day i.p.) in combination with zolmitriptan (1 mg/kg/day i.p. or 5 mg/kg/day i.p.) does not impair the ability of L-DOPA to improve motor function.

Activity Test

Locomotor activity is assessed (at day 3 of the treatment period 1) in open-field chambers, each equipped with a 16×16 infrared photobeam system (dimensions 40.6 cm×40.6 cm×38.1 cm) using the Flex-Field Software system (San Diego Instruments, San Diego, Calif.). Animals are habituated for 1 h before buspirone and zolmitriptan in the doses investigated drugs are injected and the measurements are started.

Effects on Parkinson's Disease

Stepping Test:

The stepping test (Schallert et al., 1992) is performed as described by Kirik et al., 2001 with little modifications. Briefly, the rat is held by the experimenter fixing its hindlimbs with one hand and the forelimb not to be monitored with the other, while the unrestrained forepaw is touching the table. The number of adjusting steps is counted, while the rat is moved sideways along the table surface (90 cm in 5 s), in the forehand and backhand direction, for both forelimbs, and the average of the steps in the two directions is considered. Performance of the animals in the stepping test is assessed during treatment period 1 (after training sessions and reach of a stable performance) in the L-DOPA, buspirone and zolmitriptan-treated group and in a group of naive rats, after administration of L-DOPA, buspirone and zolmitriptan+ or L-DOPA only, respectively. On the day of the test (day 5 of treatment period 1) L-DOPA, buspirone and zolmitriptan-treated and naive rats are tested twice in baseline condition and two more times 60 min after administration of the drugs. Values are reported as an average of the two sessions on and off drug. The results show that buspirone (1 mg/kg/day i.p.) in combination with zolmitriptan (1 mg/kg/day i.p. or 5 mg/kg/day) (which significantly reduce L-DOPA-induced dyskinesia) do not have significant negative effects on the treatment with L-DOPA in this model, when comparing rats treated with L-DOPA alone to rats treated with both L-DOPA and a combination of buspirone and zolmitriptan. Thus, the combination of buspirone (1 mg/kg/day i.p.) in combination with zolmitriptan (1 mg/kg/day i.p. or 5 mg/kg/day i.p.) does not impair the ability of L-DOPA to improve motor function.

Tacrine-Induced Tremulous Jaw Movements in Rats can be Used as an Experimental Model of Parkinsonian Tremor Observations of tremulous jaw movements in rats are made in a 27×17.5×17 cm clear plexiglas chamber with a wire mesh floor. Tremulous jaw movements are defined as rapid vertical deflections of the lower jaw that resemble chewing but are not directed at any particular stimulus. Each individual deflection of the jaw is recorded using a mechanical hand counter. Jaw movements are recorded by an observer who is unaware of the experimental treatment conditions, and the observer is trained to demonstrate interrater reliability with a second observer over a number of pilot test sessions (r=0.92; P<0.05). To induce tremulous jaw movements, each rat receives an i.p. injection of 5.0 mg/kg of the anticholinesterase tacrine 10 min before testing. Rats are placed in the observation chamber immediately after tacrine injection for a 10-min habituation period. The rats are subsequently observed for tremulous jaw movements during a 5-min session. The effects of buspirone in combination with zolmitriptan, 20 min before tacrine; n=11) on tacrine-induced tremulous jaw movements are evaluated. Rats are tested once a week for 5 weeks, during the light phase of the light/dark cycle. Over the course of the experiment, each rat receives all treatments in a randomly varied order. Vehicle levels of tremulous jaw movement activity are consistent across the repeated weeks of the study. The studies show that buspirone (1 mg/kg/day i.p.) in combination with zolmitriptan (1 mg/kg/day i.p. or 5 mg/kg/day) (which significantly reduce L-DOPA-induced dyskinesia), do not have negative effects on the treatment with L-DOPA in this model, when comparing rats treated with L-DOPA alone to rats treated with both L-DOPA and a combination of buspirone and zolmitriptan.

In conclusion, the combination of buspirone (1 mg/kg/day i.p.) with zolmitriptan (1 mg/kg/day i.p. or 5 mg/kg/day) gives no significant reduction in motor performance and coordination of the rat in the rotarod, stepping, or tremulous-jaw test mentioned above. Furthermore, the combination of buspirone (1 mg/kg/day i.p.) with zolmitriptan (1 mg/kg/day i.p. or 5 mg/kg/day i.p.) does not impair the beneficial effects of L-DOPA on motor performance in models of Parkinson's disease. Together this demonstrates that a combination of buspirone and zolmitriptan in doses that reduces LID (L-DOPA induced dyskinesia) in a subject, will not impair the ability of L-DOPA to reduce symptoms of Parkinson's disease, such as akinesia.

In Vivo Microdialysis and Behavior

Administration of L-DOPA to unilaterally 6-OHDA-lesioned rats induces abnormal involuntary movements (AIMs) and changes in concentrations of neurotransmitters in the brain. Using special methodologies it is possible to measure levels of such neurotransmitters (e.g. dopamine, gamma amino butyric acid (GABA), noradrenalin, serotonin) in different brain regions in freely moving rats that previously have been treated with 6-OHDA. This procedure allows for a direct comparison between central neurotransmitters and behavior and is a method used to determine mechanism of action and efficacy of compounds of the present invention.

Buspirone (1 mg/kg/day i.p.) in combination with zolmitriptan (1 mg/kg/day i.p. or 5 mg/kg/day) are shown to significantly reduce central dopamine levels as determined by this method.

PET Scanning.

The levels of neurotransmitters and receptors for such neurotransmitters in different regions of the brain of animals and humans can be determined using PET scanning. Such procedures are useful to study levels of dopamine and dopamine receptors in healthy and disease animals and humans and thereby study effects of drug treatment of Parkinson's disease. Furthermore this procedure can be used to predict effects in humans from animal studies and are useful for predicting efficacy of drug combinations of the current invention. A commonly used PET tracer for studying dopamine levels in human volunteers, in patients suffering from Parkinson's disease and in animal models of Parkinson's disease is [$^{11}$C]raclopride. Raclopride is a ligand for the dopamine D2 and D3 receptors. Using PET scanning, this tracer allows for a determination of changes in extracellular dopamine levels caused by treatment with drugs and drug combinations.

The experimental setup testing various doses of buspirone (0.5-20 mg/day i.p.) in combination with various doses of zolmitriptan (0.5-20 mg/day i.p.) shows that buspirone (1 mg/kg/day i.p.) in combination with zolmitriptan (1 mg/kg/day i.p. or 5 mg/kg/day) significantly reduces central dopamine levels as determined by this method.

Example III

Treatment of Individuals Suffering from Movement Disorders

The following illustrates an example of the use of the compounds of the invention for treatment of patient suffering from LID:

A 69 years old woman has been diagnosed with PD 6 years ago and has since then been treated with L-DOPA/carbidopa (300/75 mg given in 3 divided doses). She has started to experience involuntary movements and is diagnosed with L-DOPA induced dyskinesia. The patient is treated with a combination of buspirone (20 mg) and zolmitriptan (2.5 mg) administered orally two times a day. After 8 days of treatment, the symptoms of dyskinesia are assessed by the scales Lang-Fahn Activities of Daily Living Dyskinesia scale, Clinical Global Impression, Unified Parkinson's Disease Rating Scales as well as the Abnormal Involuntary Movement Scale (AIMS). The patient is continuously administered buspirone and zolmitriptan in the doses mentioned above.

The following illustrates an example of the use of the compounds of the invention for treatment of patient suffering from neuroleptica induced akathisia:

A 28-year-old male with schizophreniform disorder has developed akathisia following 4 days of treatment with haloperidol 10 mg/day. Akathisia is rated as 4 (marked) using the Barnes Akathisia Scale (BAS). The BAS is a validated, clinician-administered scale used to evaluate the severity of drug-induced akathisia. The patient is treated with a combination of buspirone (20 mg) and zolmitriptan (2.5 mg) administered orally two times a day. After 14 days of treatment, the BAS score is observed in order to detect changes in the akathisia related symptoms.

The following illustrates an example of the use of the compounds of the invention for treatment of patient suffering from neuroleptica induced tardive dyskinesia.

A 19 year old woman with a 12 month history of schizophrenia, developed buccolingual masticatory tardive dyskinesia (assessed with the Abnormal Involuntary Movement Scale (AIMS)) after receiving risperidone 6 mg. The patient is treated with a combination of buspirone (20 mg) and frovatriptan (1 mg) administered orally two times a day. After 3 weeks of treatment improvement in the tardive dyskinesia is assessed.

Example IV

Evaluation of 5-HT1 Agonists Buspirone and Zolmitriptan for Treatment of Movement Disorders Associated with Parkinson's Disease and LID The present study describes the evaluation of zolmitriptan and buspirone in the 6-OHDA rat model as described in Example II.

Test Procedure:

Animals: 98 Sprague-Dawley male rat (bred in house, originally from SLAC Laboratory Animal Co. Ltd) at 9-week of age at body weight of 200 to 250 g from Shanghai SLAC Co. Ltd. arrived at the laboratory at least 1 week prior to behavioural testing. Rats were housed in groups of n=2/cage. Animals had ad libitum access to standard rodent chow and water. Animal housing and testing rooms were maintained under controlled environmental conditions and were within close proximity of each other. Animal housing rooms were on a 12-hour light-dark cycle with lights on at 6:00 AM and maintained at 70° F./21° C. (range: 68-72° F./20-22° C.) with a humidity range of 20-40%. Testing rooms were maintained at 68-72° F. with a humidity range of 20-40%.

6-OHDA Lesion Surgery:

Dopamine (DA)-denervating lesions were performed by unilateral injection of 6-OHDA in the ascending nigrostriatal pathway. Rats were anesthetized with pentobarbital sodium 40 mg/kg (i.p.) and positioned in a stereotactic frame. 6-OHDA was injected into the right ascending DA bundle at the following coordinates (in mm) relative to bregma and dural surface: (1) toothbar position −2.3, A=−4.4, L=1.2, V=7.8, (7.5 ug 6-OHDA), (2) toothbar position+3.4, A=−4.0, L=0.8, V=8.0 mm (6 ug 6-OHDA). Alternatively only one injection was made with the following coordinates: Tooth bar: −3.3 mm, AP: −1.8 mm, ML: −2.0 mm, DV: −8.6 mm (18 μg/6 μg/6-OHDA). The neurotoxin injections were performed at a rate of 1 ul/min, and the injection cannula was left in place for an additional 2-3 min thereafter.

After recovery from surgery, rats with nearly complete (>90%) lesions were selected by means of an apomorphin-induced rotation test. I.p. injection of 0.5 mg/kg apomorphine.HCl (Sigma) in saline evoked contralateral turning, which is considered to be the result of de-nervated hypersensitivity of DA receptors in the lesion side. Rotational behaviour in response to DA agonists grossly correlates with the severity of the lesion. Quantification of the rotational response was accomplished in rats by counting the turns in 30 minutes. Rat with rotational score ≥6 turns/min were selected for next tests. Animals were then allocated into two well-matched sub-groups (according to the amphetamine rotation) and received daily treatment as described below.

Drugs and Treatment Regimens

L-DOPA methyl ester (Sigma, Cat No. D9628 Lot. No. 030M1604V)) was given at the dose of 6 mg/kg/day, combined with 15 mg/kg/day of benserazide HCl. Chronic treatment with this dose of L-DOPA and benserazide was given for 3 weeks or more to all the rats with good lesions in order to induce a gradual development of dyskinetic-like movements. Thereafter, rats that had not developed dyskinesia were excluded from the study, and the rats with a cumulative AIM score ≥28 points over five testing sessions (dyskinesia severity grade 2 on each axial, limb and orolingual scores) were kept on a drug treatment regimen of at least two injections of L-DOPA/benserazide per week in order to maintain stable AIM scores. The selected rats were allocated groups of 9-12 animals each, which were balanced with the respect to AIM severity. The animals were then treated with the drug and drug combinations as described below.

L-DOPA Induced AIMs and Drugs Screening Test

Rats were tested for AIMs as described above in Example II except that the sum of locomotive (LO) or axial (AX), limb (LI), and orolingual (OL) AIM scores per testing session was used for statistical analyses.

To determine the effects of specific doses of a combination of buspirone and zolmitriptan the following group setting was used:

Vehicle: (saline, i.p., 30 min before L-DOPA, n=6)

Buspirone (1 mg/kg, i.p., n=6)

Zolmitriptan (From Damas-beta, Cat. No. TSP76106 Lot. No. T4903TSP76106, 10 mg/kg, i.p. n=6)

Zolmitriptan (3 mg/kg, i.p.)+Buspirone (1 mg/kg, i.p., n=6)

Zolmitriptan (10 mg/kg, i.p.)+Buspirone (1 mg/kg, i.p., n=6)

Zolmitriptan is given 35 minutes before L-DOPA while buspirone is given 30 minutes before L-DOPA.

The results of the drug screening test are presented in FIG. 1 and showed that buspirone (1 mg/kg/day i.p.) in combination with zolmitriptan (3 mg/kg/day i.p. or 10 mg/kg/day) significantly reduced L-DOPA-induced dyskinesia. When given alone zolmitriptan (10 mg/kg/day) did not reduce AIM, while buspirone (1 mg/kg/day i.p.) only partly reduced AIM.

Example V

The present study describes the evaluation of zolmitriptan and buspirone in the 6-OHDA rat model in a study using the rotarod test. Using this study, a treatment with combination of compounds according to the present invention can be evaluated for their sedative effects, and/or their effects on the motor performance compared to sedated rats and to rats which only had saline injections.

Rotarod Test

The rotarod test serves the purpose of detecting potential deleterious effects of the compounds studied on the rats' motor performance and coordination. In brief, the animals (30 SD male rats (180-220 g, bred in house, originally from SLAC Laboratory Animal Co. Ltd) at 9-week of age) were trained twice a day for a 3-day period. The rats were placed on the accelerating rod apparatus (Shanghai Jiliang, China) at an initial speed of 4 rotations per minute (rpm), with the speed increasing gradually and automatically to 40 rpm over 300s. Each training trial was ended if the animal fell off or grips the device and spun around for two consecutive revolutions. The time that rat stayed on the Rotarod was recorded. The staying duration recorded at last training trail was used as baseline. Rats were grouped according a randomly distribution of baseline.

For the test session on the fourth day, the rats were evaluated on the Rotarod with the same setting as above at 30 min after dosing. The rats were dosed with drugs as described below. Dosing and Rotarod measurement were conducted by two scientists separately. Pentobarbital (15 mg/kg. i.p.) was used a as a positive control.

Group Setting for Compound Tests:
Vehicle: Saline, i.p., 30 min before test, n=10
Positive control: Pentobarbital 15 mg/kg, i.p. 30 min before test, n=10
Combination:
Zolmitriptan 3 mg/kg, i.p. 5 min before buspirone
Buspirone 1 mg/kg, i.p. 30 min before test, n=10

Statistical analysis: The rotarod performance is expressed as total number of seconds spent on the accelerating rod. The data were analyzed using One-Way ANOVA and the Tukey post-hoc test.

Figure 2:
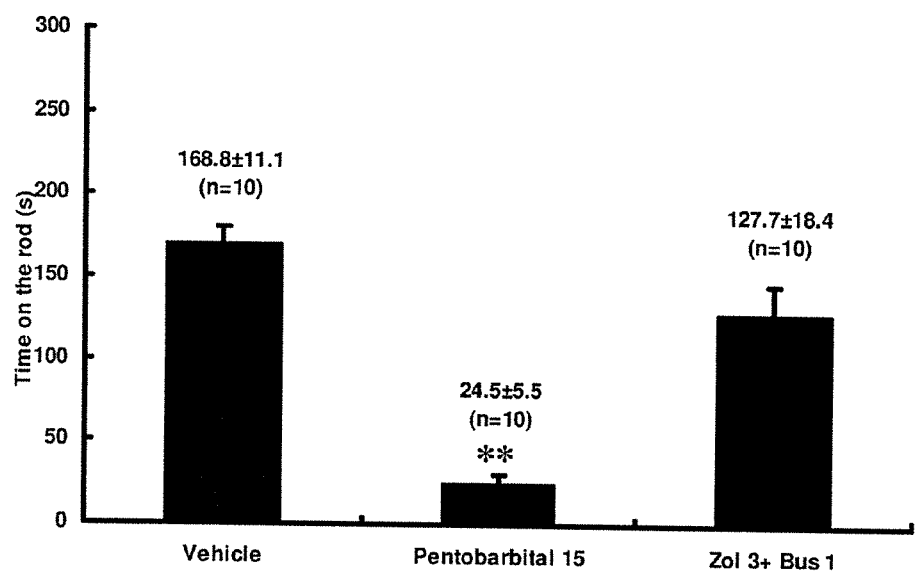
FIG. 2 shows the effect of zolmitriptan (3 mg/kg) and buspirone (1 mg/kg) on coordination of Sprague-Dawley (SD) rats in rotarod test. Asterics (**) denote effects of P<0.01 when compared with vehicle, calculated by use of the one-way ANOVA test and the Tukey post-hoc test. The first column from the left denotes rats administered vehicle only, the middle column denotes rats administered pentobarbital, and the last column from the left denotes rats administered with a combination of zolmitriptan (3 mg/kg) and buspirone (1 mg/kg). The results demonstrate that the combination of zolmitriptan (3 mg/kg) and buspirone (1 mg/kg) does not significantly induce sedation.

Result:
See FIG. 2.

Buspirone (1 mg/kg/day i.p.) in combination with zolmitriptan (3 mg/kg/day i.p.) had no statistically significant effects on performance in the rotarod model compared to rats injected with vehicle only, showing that motor performance and coordination is not significantly reduced in rats after administration of the compounds. In comparison pentobarbital significantly reduced time spend on the rotarod.

Example VI

The present study describes the evaluation of zolmitriptan and buspirone in the 6-OHDA rat model. Using this study, a treatment with combination of compounds according to the present invention can be evaluated for their sedative effects, and/or their effects on the motor performance compared to sedated rats and to rats which only had saline injections.

Open Field Test

The open field test was used to determine the effects of drug on locomotor activity. Rats were put in open-field chambers (dimensions 40 cm×40 cm) 30 minutes after dosing. After a 15 minutes habituation, locomotion were recorded and analysed by Enthovision Video Tracking Software (Noldus Information Technology, Netherlands) for 60 minutes. All locomotor activities were done during dark phase and to eliminate olfactory cues, the arena was thoroughly cleaned with 70% v/v ethanol between each test.

Group Setting for Compound Tests:
Vehicle: Saline, i.p., 30 min before test, n=10
Positive control: Pentobarbital 15 mg/kg, i.p. 30 min before test, n=10
Combination:
Zolmitriptan 3 mg/kg, i.p. 5 min before buspirone
Buspirone 1 mg/kg, i.p. 30 min before test, n=10

Statistical analysis: The total locomotor activity is expressed as total moved distance (cm) and average velocity (cm/s) during 60 minutes. The data were analysed using One-Way ANOVA and the Tukey post-hoc test. The locomotor activity in six time point is expressed as moved distance (cm) and average velocity (cm/s) every 10 minutes. The data were analysed using One-Way ANOVA and the Tukey post-hoc test in each time point.

Figure 3:
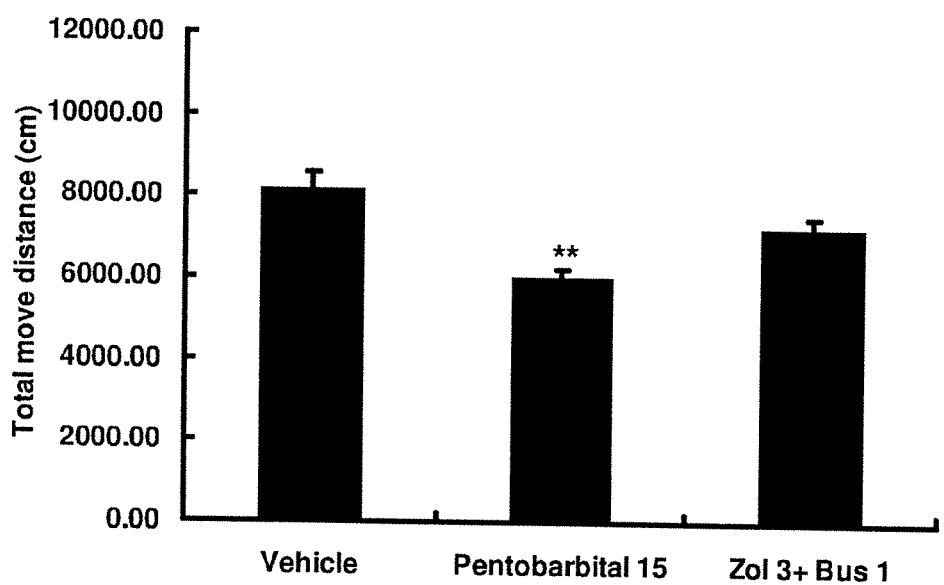
FIG. 3 shows the effect of zolmitriptan (3 mg/kg)+ buspirone (1 mg/kg) on total move distance of naïve rats in open field test. Asterics (**) denote effects of P<0.01 when compared with vehicle, calculated by use of the one-way ANOVA test and the Tukey post-hoc test. The first column from the left denotes rats administered vehicle only, the middle column denotes rats administered pentobarbital, and the last column from the left denotes rats administered with a combination of zolmitriptan (3 mg/kg) and buspirone (1 mg/kg). The results demonstrate that the combination of zolmitriptan (3 mg/kg) and buspirone (1 mg/kg) does not significantly induce sedation.

Result:
See FIG. 3.

A treatment with buspirone (1 mg/kg/day i.p.) in combination with zolmitriptan (3 mg/kg/day i.p.) had no statistically significant effects on performance in the open field test compared to rats injected with vehicle only as measured during the 30 minutes observation period. Pentobarbital significantly reduced motor performance during the total observation period.

Example VII

L-DOPA Induced AIMs and Drugs Screening Test

Rats were tested for AIMs as described above in Example II except that the sum of locomotive (LO) oraxial (AX), limb (LI), and orolingual (OL) AIM scores per testing session was used for statistical analyses. To determine the effects of specific doses of a combination of buspirone and zolmitriptan the following group setting was used:
Vehicle: (saline, i.p., 30 min before L-DOPA, n=6)
Buspirone (0.5 mg/kg, intra peritoneally (i.p.), n=6)
Buspirone (0.5 mg/kg i.p.)+Zolmitriptan (From Damas-beta, Cat. No. TSP76106 Lot. No. T4903TSP76106, 3 mg/kg i.p.)
Buspirone (0.5 mg/kg i.p.)+Zolmitriptan (10 mg/kg i.p.)
Buspirone (1 mg/kg i.p.)+Zolmitriptan (10 mg/kg i.p.)
Zolmitriptan was given 35 minutes before L-DOPA while buspirone was given 30 minutes before L-DOPA.

Figure 4:
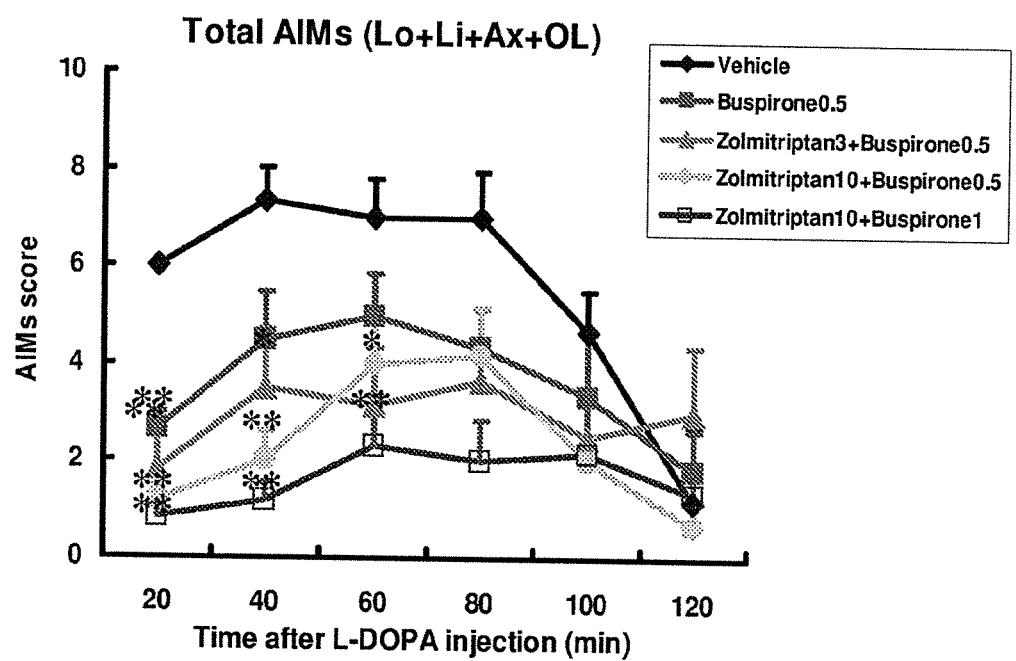
FIG. 4 shows the effect of combination of buspirone and zolmitriptan on L-DOPA induced abnormal involuntary movements (AIMs) in rats (Total AIMs=sum of locomotive (LO) oraxial (AX), limb (LI), and orolingual (OL) AIM scores). Asterics (**) denote effects of P<0.01 compared with vehicle calculated by use of the one-way ANOVA test and the Tukey post-hoc test in each time point. Zolmitriptan was given 35 minutes before L-DOPA while buspirone was given 30 minutes before L-DOPA. Diamonds denote rats administered vehicle only, filled square denote rats administered 0.5 mg/kg buspirone, triangles denote rats administered 3 mg/kg zolmitriptan in combination with 0.5 mg/kg buspirone, filled circles denote rats administered 10 mg/kg zolmitriptan in combination with 0.5 mg/kg buspirone and open squares denote rats administered 10 mg/kg zolmitriptan in combination with 1 mg/kg buspirone. The curves show different treatments: buspirone (0.5 mg/kg); buspirone (0.5 mg/kg)+zolmitriptan (3 mg/kg); buspirone (0.5 mg/kg)+zolmitriptan (10 mg/kg) and buspirone (1 mg/kg)+ zolmitriptan (10 mg/kg).

The results of the drug screening test are presented in FIG. 4 and showed that buspirone (0.5 mg/kg i.p.) in combination with zolmitriptan (3 mg/kg i.p. or 10 mg/kg i.p) or buspirone (1.0 mg/kg i.p.) in combination with zolmitriptan (10 mg/kg i.p) significantly reduced L-DOPA-induced dyskinesia. When given alone buspirone (0.5 mg/kg i.p.) only partly reduced AIM.

Example VIII

Forepaw Adjusting Steps (FAS)

The FAS test (Schallert et al., 1992, Olsson et al., J Neurosci; 15:3863-75, 1995) has been extensively utilized as a measure of forelimb akinesia, demonstrating sensitivity to DA loss and reversal of deficit by DA replacement therapy.

Test Procedure:
Animals: 60 Sprague-Dawley male rats (290 g-340 g, bought from SLAC Laboratory Animal Co. Ltd at an age of 8-10 weeks). Rats were housed in groups of n=2/cage. Animals had ad libitum access to standard rodent chow and water. Animal housing and testing rooms were maintained under controlled environmental conditions and were within close proximity of each other. Animal housing rooms were on a 12-hour light-dark cycle with lights on at 6:00 AM and maintained at 70° F./21° C. (range: 68-72° F./20-22° C.) with a humidity range of 20-40%. Testing rooms were maintained at 68-72° F. with a humidity range of 20-40%.

6-OHDA Lesion Surgery:
Dopamine (DA)-denervating lesions were performed by unilateral injection of 6-OHDA in the median forebrain bundle containing the ascending nigrostraital pathway. Rats were anesthetized with pentobarbital sodium 40 mg/kg (i.p.) and positioned in a stereotactic frame. 6-OHDA was injected at the following coordinates (in mm) relative to bregma and dural surface: Tooth bar: −3.3 mm, AP: −1.8 mm, ML: −2.0 mm, DV: −8.6 mm (18 μg/6 μl 6-OHDA). The neurotoxin injections were performed at a rate of 0.5 μl/min, and the injection cannula was left in place for an additional 2-3 min thereafter.

After recovery from surgery, rats with nearly complete (>90%) lesions were selected by means of an apomorphin-induced rotation test. I.p. injection of 0.5 mg/kg apomorphine.HCl (Sigma) in saline evoked contralateral turning, which is considered to be the result of hypersensitivity of DA receptors in the lesion side. Rotational behaviour in response to DA agonists grossly correlates with the severity of the lesion. Quantification of the rotational response was accomplished in rats by counting the turns in 30 minutes. Rats with rotational counts ≥180 turns in 30 minutes were elected for next tests. Animals were then allocated into two well-matched sub-groups (according to the apomorphine rotation) and received daily treatment with L-DOPA.

Drugs and Treatment Regimens

The 6-OHDA unilateral lesion model rats (600 g-630 g, 25-week of age, husbandried in house) were used in the study.

Initially baseline was established by the following procedure. All the test animals were habituated by the experimenter to grip. The rat was trained to run spontaneously up the ramp to the home cage with its ungriped paw. Adjusting steps of each rat were consisted of moving in two directions (forehand and backhand).

Each baseline adjusting step test consisted of two subtests of the day and the mean of the two subtests were calculated as baseline.

Forty animals, which had the baseline test in the model, were used in the combination study with zolmitriptan (Damas-beta, Cat No. TSP76106, Lot. No. T4903TSP76106), buspirone (Sigma, Cat. No. B7148, Lot. No. 042K1763Z) and L-DOPA (Sigma, Cat No. D9628, Lot. No. 030M1604V. L-DOPA and benzerazide was dissolved in saline (vehicle 1) while buspirone and zolmitriptan were dissolved in 10% tween-80 (vehicle 2).

Group Setting for Compound Tests:
1) Vehicle 1 (saline) with 15 mg/kg benserazide HCl (s.c. 60 min pretest)+Vehicle 2 (10% tween-80, i.p., 30 min pretest)+ Vehicle 2 (10% tween-80, i.p., 30 min pretest, n=14).
2) L-DOPA 3 mg/kg with 15 mg/kg benserazide HCl(s.c. 60 min pretest,)+Vehicle 2 (10% tween-80, i.p., 30 min pretest)+Vehicle 2 (10% tween-80, i.p., 30 min pretest, n=14).
3) L-DOPA 3 mg/kg with 15 mg/kg benserazide (s.c. 60 min pretest)+0.5 mg/kg buspirone (i.p., 30 min pretest)+10 mg/kg zolmitriptan (i.p., 30 min pretest, n=14)

The test rats were allocated randomly to 3 groups, which were balanced with the respect to the baseline test.

All the test animals were habituated by the experimenter to grip. The rat was trained to run spontaneously up the ramp to the home cage with its ungriped paw.

Adjusting steps of each rat were consisted of moving in two directions (forehand and backhand).

Each baseline adjusting step test consisted of two subtests of the day and the mean of the two subtests were calculated as baseline.

Data was presented as percentage of adjusting step of impaired paw to intact paw. This calculation indicates the degree of forepaw disability.

It was found that acute treatment of 3 mg/kg L-DOPA (with 15 mg/kg benserazide) alleviated 6-OHDA induced akinesia by increasing the forelimb use. An acute co-administration of buspirone (0.5 mg/kg)+zolmitriptan (10 mg/kg) did not change the effect of L-DOPA (3 mg/kg with 15 mg/kg benserazide) on 6-OHDA induced akinesia.

The average percentage of adjusting steps in each groups were calculated as: Vehicle: 64.4%
L-DOPA (3 mg/kg with 15 mg/kg benserazide): 77.8%
L-DOPA (3 mg/kg with 15 mg/kg benserazide) plus buspirone (0.5 mg/kg)+zolmitriptan (10 mg/kg): 77.9%

To study the effects of a combination of buspirone (0.5 mg/kg)+zolmitriptan (10 mg/kg) without co-administration of L-DOPA the following groups were examined:
1) Vehicle 1 with 15 mg/kg benserazide HCl (s.c., 60 min pretest)+Vehicle 2, (i.p., 30 min pretest)+Vehicle 2 (i.p., 30 min pretest, n=10).
2) 3 mg/kg L-DOPA with 15 mg/kg benserazide HCl (s.c., 60 min pretest)+Vehicle 2 (i.p., 30 min pretest)+Vehicle 2 (30 min pretest, n=10). n=10).
3) Vehicle 1 with 15 mg/kg benserazide (s.c. 60 min pretest)+0.5 mg/kg buspirone (i.p., 30 min pretest)+10 mg/kg zolmitriptan (i.p., 30 min pretest, n=10).

It was found that 3 mg/kg L-DOPA with 15 mg/kg benserazide HCl significantly increase the forelimb use. The effect of buspirone (0.5 mg/kg)+zolmitriptan (10 mg/kg) on forelimb use was not significantly different from L-DOPA.

The average percentage of adjusting steps in each groups were calculated as:
Vehicle: 69.5%
L-DOPA (3 mg/kg with 15 mg/kg benserazide): 77.7%
Buspirone (0.5 mg/kg)+zolmitriptan (10 mg/kg): 82.0%

The results show that a combination of buspirone and zolmitriptan in doses that are able to reduce abnormal involuntary movements in a rat model of L-DOPA induced dyskinesia do not impair the effects of L-DOPA on akinesia.

This further demonstrates that a combination of buspirone and zolmitriptan could reduce L-DOPA induced dyskinesia in patients suffering from Parkinson's disease without affecting the beneficial effects of L-DOPA. Furthermore that data demonstrate that combination of buspirone and zolmitriptan alone has a beneficial effect on symptoms of Parkinson's disease.

Example IX

Effects of Compounds in Rat Model of Tardive Dyskinesia

Zolmitriptan given in combination with buspirone, was evaluated for possible activity against reserpine-induced tardive dyskinesia in mice. Reserpine at 1 mg/kg was injected subcutaneously (s.c.) to induce tardive dyskinesia on days 1 and 3. Combinations of zolmitriptan with buspirone were given intraperitoneally (i.p.) 24 hours following the 2nd reserpine injection. VCM (vacuous chewing movements) were measured for 10 minutes, 1 hour after the 2nd injection of test compounds on day 4. Buspirone and zolmitriptan dissolved/suspended in 20% Tween 20/0.9% NaCl were administered intraperitoneally with a dosing volume of 10 mL/kg. All the test substances were prepared freshly before use.

Male ICR mice weighing 36±2 g were obtained from BioLasco Taiwan, a Charles River Laboratories Technology Licensee. The animals were housed in animal cages with a space allocation of 29×18×13 cm for 5 mice. All animals were maintained in a hygienic environment under controlled temperature (20° C.-24° C.), humidity (50%-80%) with 12 hours light/dark cycles for at least three days prior to use in Ricerca Taiwan, Ltd. laboratory. Free access to standard lab chow [MF-18 (Oriental Yeast Co., Ltd., Japan)] and tap water was granted. All aspects of this work including housing, experimentation and disposal of animals were performed in general accordance with the Guide for the Care and Use of Laboratory Animals (National Academy Press, Washington, D.C., 1996).

Groups of 10 male ICR mice weighing 36±2 g (at arrival) were used. All animals were challenge with 1st dose of reserpine (1 mg/kg s.c.) on day 1, followed by 2nd dosing of reserpine separated by 48 hours on day 3 to induce tardive dyskinesia. Vehicle and test articles were injected intraperitoneally 24 hours post the 2nd challenge of reserpine on day 4. One hour after dosing of the 2nd article, behavioural observations were carried out for vacuous chewing movements.

For the behavioral assessment, animals were individually placed in a plexiglass cage (13 cm×23 cm×13 cm). Mirrors were placed under the floor of the cage to permit observation of oral movements when the animals faced away from the observer. After a 5 min period of habituation, the occurrence of vacuous chewing movements (VCM) was counted for a further 10 min period. VCM were referred to as single mouth openings in the vertical plane not directed toward physical material. If VCM occurred during a period of grooming, they were not taken into account.

The total number of VCM each group was recorded and the mean±SEM for each group was determined. One-way ANOVA followed by Dunnett's test was applied for comparison between vehicle control and treated groups. Differences are considered significant at $P<0.05$ (*).

The number of VCM's for the different test groups were (mean±SEM):
Vehicle (36.7±6.7);
Buspirone (3 mg/kg i.p.) plus zolmitriptan (30 mg/kg i.p.): (7.3±4.6)*.

In conclusion it was found that buspirone in combination with zolmitriptan significantly reduce reserpine induced tardive dyskinesia in mice.

Items

The following items additionally serve to describe the present invention:

1. A pharmaceutical composition comprising at least one compound, wherein said compound is either an agonist of two or more of the serotonin receptors selected from the group of
   5-HT1B
   5-HT1D
   5-HT1F
   receptors, or a selective agonist of the 5-HT1D receptor, or a selective agonist of the 5-HT1F receptor, or a pharmaceutically acceptable derivative thereof, and wherein said composition further comprises a 5-HT1A agonist or a pharmaceutically acceptable derivative thereof, for treatment, prevention or alleviation of movement disorders.
2. The pharmaceutical composition according to item 1 wherein the compound is an agonist of the 5-HT1B receptor and 5-HT1D receptor or a pharmaceutically acceptable derivative thereof.
3. The pharmaceutical composition according to the previous items, wherein the compound is a selective agonist of the 5-HT1D receptor, or a selective agonist of the 5-HT1F receptor, or a pharmaceutically acceptable derivative thereof.
4. The pharmaceutical composition according to the previous items, wherein the compound is an agonist of the 5-HT1B receptor, the 5-HT1D receptor and the 5-HT1F receptor, or a pharmaceutically acceptable derivative thereof
5. The pharmaceutical composition according to the previous items wherein the compound has higher affinity and/or receptor activation efficacy of the 5-HT1D receptor compared to the 5-HT1B receptor.
6. The pharmaceutical composition according to the previous items wherein the compound has higher affinity and/or receptor activation efficacy for the 5-HT1D receptor compared to the 5-HT1B and 5-HT1F receptors.
7. The pharmaceutical composition according to the previous items wherein the compound is selected from the group of sumatriptan, zolmitriptan, rizatriptan, naratriptan, almotriptan, frovatriptan and eletriptan or pharmaceutically acceptable derivatives thereof
8. The pharmaceutical composition according to the previous items wherein the compound is COL-144, LY334370, LY344864, or a pharmaceutically acceptable derivative thereof
9. The pharmaceutical composition according to the previous items wherein the compound is administered in doses of 0.05-200 mg/day.
10. The pharmaceutical composition according to the previous items wherein the compound is administered in doses of 0.5-60 mg/day, such as in doses of 0.5-10 mg/day.
11. The pharmaceutical composition according to the previous items wherein the compound is administered in single doses of 0.05-100 mg/kg bodyweight.
12. The pharmaceutical composition according to the previous items wherein the 5-HT1A agonist is selected from the group of alnespirone, binospirone, buspirone, gepirone, ipsapirone, perospirone, tandospirone, befiradol, repinotan piclozotan, osemozotan, flesinoxan, flibanserin and sarizotan or a pharmaceutically acceptable derivative thereof.
13. The pharmaceutical composition according to the previous items wherein the 5-HT1A agonist is tandospirone, gepirone or buspirone or a pharmaceutically acceptable derivative thereof.
14. The pharmaceutical composition according to the previous items wherein compound is selected from the group of zolmitriptan and frovatriptan or a pharmaceutically acceptable derivative thereof, and the 5-HT1A receptor agonist is selected from buspirone, tandospirone or gepirone or a pharmaceutically acceptable derivative thereof.
15. The pharmaceutical composition according to the previous items wherein the compound is zolmitriptan or a pharmaceutically acceptable derivative thereof and the 5-HT1A agonist is buspirone or a pharmaceutically acceptable derivative thereof.
16. The pharmaceutical composition according to previous items wherein the 5-HT1A agonist is administered in doses of 0.05-500 mg/day.
17. The pharmaceutical composition according to the previous items wherein the 5-HT1A agonist is administered in doses of 0.5-100 mg/day, such as in doses of 0.5-30 mg/day.
18. The pharmaceutical composition according to the previous items wherein the 5-HT1A agonist is administered in doses of 0.5-100 mg/day and the compound is administered in doses of 0.5-60 mg/day, such as wherein the 5-HT1A agonist is administered in doses of 0.5-30 mg/day and the compound is administered in doses of 0.5-10 mg/day.
19. The pharmaceutical composition according to previous items wherein the 5-HT1A agonist is administered in single doses of 0.05-100 mg/kg bodyweight.
20. The pharmaceutical composition according to the previous items further comprising one or more second active ingredients.
21. The pharmaceutical composition according to the previous items further comprising one or more second active ingredients selected from the group of agents increasing the dopamine concentration in the synaptic cleft, dopamine, L-DOPA or dopamine receptor agonists or a pharmaceutically acceptable derivative thereof.
22. The pharmaceutical composition according to the previous items further comprising one or more second active ingredients selected from the group of agents which ameliorate symptoms of Parkinson's disease or which are used for treatment of Parkinson's disease.
23. The pharmaceutical composition according to the previous items wherein the compound is zolmitriptan or a pharmaceutically acceptable derivative thereof and the 5-HT1A agonist is buspirone or a pharmaceutically acceptable derivative thereof further comprising L-DOPA or a pharmaceutically acceptable derivative thereof.
24. The pharmaceutical composition according to the previous items further comprising two or more second active ingredients wherein one is L-DOPA and the other is a decarboxylase inhibitor, such as carbidopa or benserazide.
25. The pharmaceutical composition according to item 24 wherein the decarboxylase inhibitor is carbidopa or benserazide.
26. The pharmaceutical composition according to the previous items further comprising two or more second active ingredients wherein one is L-DOPA and the other is a COMT inhibitor.
27. The pharmaceutical composition according to item 26 wherein the COMT inhibitor is tolcapone, or entacapone.
28. The pharmaceutical composition according to the previous items wherein the movement disorder is a movement disorder associated with altered synaptic dopamine levels.
29. The pharmaceutical composition according to the previous items wherein the movement disorder is one or more disorders selected from group of tarditive dyskinesia, akathisia, Parkinson's disease, movement disorders associated with Parkinson's disease, such as bradykinesia, akinesia and dyskinesia such as L-DOPA induced dyskinesia.
30. The pharmaceutical composition according to the previous items wherein the movement disorder is one or more disorders selected from the group of Parkinson's disease, movement disorders associated with Parkinson's disease, such as akinesia, and bardykinesia and dyskinesia such as L-DOPA induced dyskinesia.
31. The pharmaceutical composition according to the previous items wherein the movement disorder is dyskinesia associated with Parkinson's disease, such as L-DOPA induced dyskinesia.
32. The pharmaceutical composition according to the previous items wherein the movement disorder is tardive dyskinesia.
33. The pharmaceutical composition according to the previous items formulated for parenteral administration.
34. The pharmaceutical composition according to the previous items formulated for enteral administration such as oral administration.
35. The pharmaceutical composition according to the previous items formulated for crossing the blood-brain barrier.
36. A compound for treatment, prevention or alleviation of movement disorders, wherein said compound is as defined in any of the items 1 to 35.
37. A method for treatment, prevention or alleviation of movement disorders comprising one or more steps of administration of an effective amount of a pharmaceutical composition or a compound as defined in any of the items 1 to 35 to an individual in need thereof.
38. The method according to item 37 wherein the compound as defined in any of the items 1 to 35 is administered in doses of 0.05 mg/day to 200 mg/day.
39. The method according to items 37 to 38 wherein the compound as defined in any of the items 1 to 35 is administered in doses of 0.5 mg/day to 60 mg/day, such as in doses of 0.5 mg/day to 10 mg/day.
40. The method according to items 37 to 39 further comprising a step of simultaneous, sequential or separate administration of a effective amount of one or more second active ingredients.
41. The method according to items 37 to 39 wherein the compound as defined in items 1 to 35 is administered simultaneously, sequentially or separately in combination with an effective amount of a 5-HT1A agonist.
42. The method according to items 37 to 41 wherein the compound as defined in items 1 to 35 is administered simultaneously, sequentially or separately in combination with an effective amount of a 5-HT1A agonist selected from the group of alnespirone, binospirone, buspirone, gepirone, ipsapirone, perospirone, tandospirone, befiradol, repinotan, piclozotan, osemozotan, flesinoxan, flibanserin and sarizotan or a pharmaceutically acceptable derivative thereof.
43. The method according to items 40 to 42 wherein the 5-HT1A agonist is selected from buspirone, gepirone or tandospirone or a pharmaceutically acceptable derivative thereof.
44. The method according to items 40 to 43 wherein the 5-HT1A agonist is administered in doses of 0.05 mg/day to 500 mg/day.
45. The method according to items 40 to 44 wherein the 5-HT1A agonist is administered in doses of 0.5 mg/day to 100 mg/day, such as in doses of 0.5 mg/day to 30 mg/day.
46. The method according to items 35 to 45, wherein the pharmaceutical composition or compound as defined in items 1 to 35 is administered simultaneously, sequentially or separately in combination with one or more second active ingredients selected from the group of agents increasing the dopamine concentration in the synaptic cleft, dopamine, L-DOPA or dopamine receptor agonists or a pharmaceutically acceptable derivative thereof.
47. A kit of parts comprising the pharmaceutical composition or compound as defined in items 1 to 35 for treatment, prevention or alleviation of movement disorders.
48. The kit of parts according to item 47 further comprising one or more second active ingredients for simultaneous, sequential or separate administration.
49. The kit of parts according to items 47 to 48 further comprising a 5-HT1A agonist.
50. The kit of parts according to item 49 further comprising a 5-HT1A agonist selected from the group of alnespirone, binospirone, buspirone, gepirone, ipsapirone, perospirone, tandospirone, befiradol, repinotan piclozotan, osemozotan, flesinoxan, flibanserin and sarizotan or a pharmaceutically acceptable derivative thereof.

51. The kit of parts according to items 49 to 50 wherein the 5-HT1A agonist is gepirone, tandospirone or buspirone or a pharmaceutically acceptable derivative thereof.

52. The kit of parts according to items 48 to 51 further comprising an agent increasing the dopamine concentration in the synaptic cleft, dopamine, L-DOPA, dopamine receptor agonists or a pharmaceutically acceptable derivative thereof.

53. A method for preparation of a pharmaceutical composition according to items 1 to 35.

REFERENCES

Bonifati et al., *Clin NeurPharmacol*, 1994, 17, 73-82.
Dekundy et al: Behavioural Brain Research 179 (2007) 76-89
Del Sorbo and Albanese: *J Neurol.* 2008; 255 Suppl 4: 32-41.
Elangbam et al: J Histochem Cytochem 53:671-677, 2005
Filip et al. *Pharmacol. Reports.* (2009) 61, 761-777; Ohno, *Central Nervous System Agents in Medicinal Chemistry,* 2010, 10, 148-157.
Fox et al: *Movement Disorders Vol.* 24, No. 9, 2009.
Grégoire et al: *Parkinsonism Relat Disord.* 2009; 15(6): 445-52.
Jenner: *Nat Rev Neurosci.* 2008; 9(9): 665-77.
Kirik et al.: J. Neurosci 2001; 21:2889-96
Ludwig et al: Clin Neuropharmacol. 1986; 9(4):373-8
Moss et al: J Clin Psychopharmacol. 1993 Jun.; 13(3):204-9.
Muñoz et al: Brain. 2008; 131(Pt 12): 3380-94
Muñoz et al: Experimental Neurology 219 (2009) 298-307.
Newman-Tancredi: Current Opinion in Investigational Drugs 2010 11(7):802-812.
Olsson et al., J Neurosci; 15:3863-75, 1995
Ohno, Central Nervous System Agents in Medicinal Chemistry, 2010, 10, 148-157
Remington: The Science and Practice of Pharmacy, 20$^{th}$ Edition, Gennaro, Ed., Mack Publishing Co., Easton, Pa., 2000
Roppongi et al: Prog Neuropsychopharmacol Biol Psychiatry. 2007; 31(1):308-10.
Schallert et al., J. Neural Transpl Plast 1992; 3:332-3

The invention claimed is:

1. A method for treatment or alleviation of a movement disorder selected from the group consisting of: ataxia, dystonia, Huntington's disease, Rett syndrome, Tourette syndrome, Wilson's disease, Machado-Joseph disease, restless leg syndrome and spasmodic torticollis, comprising: one or more steps of administration of a synergistically effective amount of a pharmaceutical composition comprising zolmitriptan or a pharmaceutically acceptable salt thereof, and
one or more steps of administration of a synergistically effective amount of buspirone a pharmaceutically acceptable salt thereof, to an individual in need thereof.

2. The method according to claim 1, wherein the zolmitriptan is administered in doses of 0.5-60 mg/day.

3. The method according to claim 1, wherein the buspirone is administered in doses of 0.5-100 mg/day.

4. The method according to claim 1, wherein said pharmaceutical composition further comprises one or more additional active ingredients.

5. The method according to claim 4, wherein said one or more additional active ingredients are selected from the group consisting of: an agent increasing the dopamine concentration in the synaptic cleft, dopamine L-DOPA and dopamine receptor agonists; agents which ameliorate symptoms of Parkinson's disease and an agent which is used for treatment of Parkinson's disease, decarboxylase inhibitors, COMT inhibitors, NMDA antagonists, MAO-B inhibitors, serotonin receptor modulators, kappa opioid receptor agonists, GABA modulators, modulators of neuronal potassium channels, glutamate receptor modulators and L-DOPA.

6. The method according to claim 5, wherein said agent increasing the dopamine concentration in the synaptic cleft is selected from the group consisting of dopamine, L-DOPA and dopamine receptor agonists.

7. The method according to claim 5, wherein said agent which is used for treatment of Parkinson's disease is selected from the group consisting of decarboxylase inhibitors, COMT inhibitors, NMDA antagonists, MAO-B inhibitors, serotonin receptor modulators, kappa opioid receptor agonists, GABA modulators, modulators of neuronal potassium channels, glutamate receptor modulators and L-DOPA.

8. The method according to claim 4, wherein the one or more additional active ingredients comprises L-DOPA, or a pharmaceutically acceptable derivative thereof.

9. The method according to claim 4, wherein said pharmaceutical composition further comprises two or more additional active ingredients, wherein at least one of the additional active ingredients is L-DOPA and wherein at least one of the additional active ingredients is a decarboxylase inhibitor or a COMT inhibitor.

10. The method according to claim 9, wherein the decarboxylase inhibitor is carbidopa or benserazide.

11. The method according to claim 9, wherein the COMT inhibitor is tolcapone or entacapone.

* * * * *